United States Patent
Braish et al.

(10) Patent No.: US 11,981,696 B2
(45) Date of Patent: May 14, 2024

(54) FLUORO-PYRIDINONE PHOSPHATES AND BORONATES USEFUL AS ANTIBACTERIAL AGENTS

(71) Applicant: Pfizer Inc., New York, NY (US)

(72) Inventors: Tamim Fehme Braish, Groton, CT (US); Matthew Frank Brown, Stonington, CT (US); Ye Che, Niantic, CT (US); Richard Andrew Ewin, Kalamazoo, MI (US); Timothy Allan Johnson, Vicksburg, MI (US); Michael Joseph Melnick, Portage, MI (US); Justin Ian Montgomery, Ledyard, CT (US); Mark Stephen Plummer, Westbrook, CT (US); Loren Michael Price, Pensacola, FL (US); Usa Reilly, New Haven, CT (US); Daniel Uccello, Colchester, CT (US)

(73) Assignee: Pfizer Inc., New York, NY (US)

( * ) Notice: Subject to any disclaimer, the term of this patent is extended or adjusted under 35 U.S.C. 154(b) by 912 days.

(21) Appl. No.: 16/980,616

(22) PCT Filed: Mar. 14, 2019

(86) PCT No.: PCT/IB2019/052082
§ 371 (c)(1),
(2) Date: Sep. 14, 2020

(87) PCT Pub. No.: WO2019/175828
PCT Pub. Date: Sep. 19, 2019

(65) Prior Publication Data
US 2021/0017205 A1   Jan. 21, 2021

Related U.S. Application Data

(60) Provisional application No. 62/643,294, filed on Mar. 15, 2018.

(51) Int. Cl.
C07F 9/58 (2006.01)
A61P 31/04 (2006.01)
C07F 5/02 (2006.01)

(52) U.S. Cl.
CPC .............. *C07F 9/58* (2013.01); *A61P 31/04* (2018.01); *C07F 5/022* (2013.01)

(58) Field of Classification Search
CPC .................................. C07F 9/58; A61P 31/04
See application file for complete search history.

(56) References Cited

FOREIGN PATENT DOCUMENTS

WO   2012120397   9/2012

OTHER PUBLICATIONS

International Written Opinion and Search Report dated May 16, 2019 for Application No. PCT/IB2019/052082, filed on Mar. 14, 2019, 11 pages.
International Preliminary Report of Patentability for Application No. PCT/IB2019/052082, filed on Mar. 14, 2019, dated Sep. 25, 202, 5 pages.

*Primary Examiner* — Shobha Kantamneni
(74) *Attorney, Agent, or Firm* — John A. Wichtowski

(57) ABSTRACT

The present invention is directed to a new fluoro-pyridinone hydroxamic acid phosphates and boronates of Formulae I, II and III

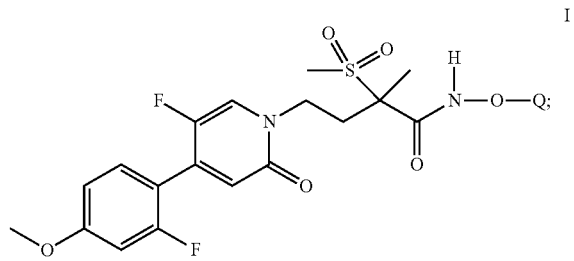

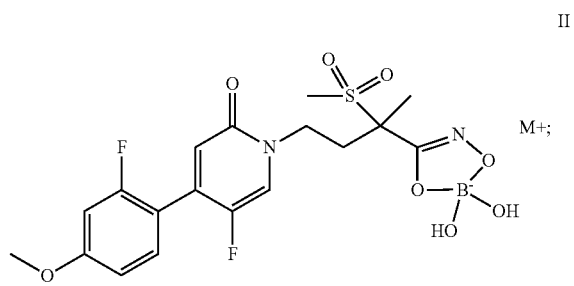

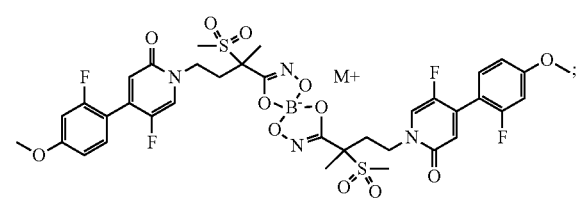

wherein Q is selected from the group consisting of —P(O)(OH)$_2$, —P(O)(OH)(O$^-$M$^+$), —P(O)(O$^-$M$^+$)$_2$ and —P(O)(O$^-$)$_2$M$^{2+}$; M$^+$ at each occurrence is a pharmaceutically acceptable monovalent cation; and M$^{2+}$ is a pharmaceutically acceptable divalent cation and their use as LpxC inhibitors and, more specifically, their use to treat bacterial infections.

18 Claims, No Drawings

FLUORO-PYRIDINONE PHOSPHATES AND BORONATES USEFUL AS ANTIBACTERIAL AGENTS

This application is a national stage application under 35 U.S.C. 371 of PCT/IB2019/052082, filed on Mar. 14, 2019, which claims the benefit of U.S. Provisional Patent Application No. 62/643,294, filed on Mar. 15, 2018, the disclosures of which are hereby incorporated by reference in their entirety.

FIELD OF THE INVENTION

This invention relates to novel fluoro-pyridinone hydroxamic acid phosphates and boronates. The invention also relates to methods of using such compounds in the treatment of bacterial infections (especially Gram-negative infections) and to pharmaceutical compositions containing such compounds.

BACKGROUND OF THE INVENTION

Infection by Gram-negative bacteria such as *Pseudomonas aeruginosa*, Extended Spectrum β-lactamase producing (ESBL) Entgerobacteriaceae, and *Acinetobacter baumannii* is a major health problem, especially in the case of hospital-acquired infections. In addition, there is an increasing level of resistance to current antibiotic therapies, which severely limits treatment options. For example, in 2002, 33% of *Pseudomonas aeruginosa* infections from intensive care units were resistant to fluoroquinolones, while resistance to imipenem was 22% (CID 42: 657-68, 2006). In addition, multi-drug resistant (MDR) infections are also increasing; in the case of *Pseudomonas aeruginosa*, MDR increased from 4% in 1992 to 14% in 2002 (Biochem Pharm 71: 991, 2006).

Gram-negative bacteria are unique in that their outer membrane contains lipopolysaccharide (LPS), which is crucial for maintaining membrane integrity, and is essential for bacterial viability (reviewed in Ann. Rev. Biochem 76: 295-329, 2007). The major lipid component of LPS is Lipid A, and inhibition of Lipid A biosynthesis is lethal to bacteria. Lipid A is synthesized on the cytoplasmic surface of the bacterial inner membrane via a pathway that consists of nine different enzymes. These enzymes are highly conserved in most Gram-negative bacteria. LpxC [UDP-3-O—(R-3-hydroxymyristoyl)-N-acetylglucosamine deacetylase] is the enzyme that catalyzes the first committed step in the Lipid A biosynthetic pathway, the removal of the N-acetyl group of UDP-3-O—(R-3-hydroxymyristoyl)-N-acetylglucosamine. LpxC is a $Zn^{2+}$-dependent enzyme that has no mammalian homologue, making it a good target for the development of novel antibiotics. Several inhibitors of LpxC with low nM affinity have been reported (Biochemistry 45: 7940-48, 2006).

SUMMARY OF THE INVENTION

The present invention is directed to certain novel 4-(5-fluoro-4-(2-fluoro-4-methoxyphenyl)-2-oxopyridin-1(2H)-yl)-2-methyl-2-(methylsulfonyl)butanamido phosphates and boronates, pharmaceutical compositions comprising those compounds and methods of inhibiting LpxC and treating bacterial infections with those compounds.

A first embodiment of a first aspect of the present invention is a new phosphate LpxC inhibitor compound, 4-(5-fluoro-4-(2-fluoro-4-methoxyphenyl)-2-oxopyridin-1(2H)-yl)-2-methyl-2-(methylsulfonyl)butanamido phosphate, or a pharmaceutically acceptable salt thereof. This compound is represented by Formula I below:

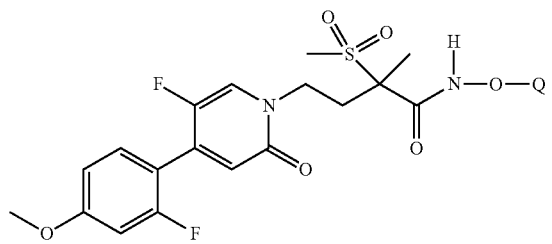

I wherein Q is a group selected from —P(O)(OH)$_2$, —P(O)(OH)(O$^-$M$^+$), —P(O)(O$^-$M$^+$)$_2$ and —P(O)(O$^-$)$_2$M$^{2+}$; M$^+$ at each occurrence is a pharmaceutically acceptable monovalent cation; and M$^{2+}$ is a pharmaceutically acceptable divalent cation.

A first embodiment of a second aspect of the present invention is the new boronate Lpxc inhibitor compound of the formula II

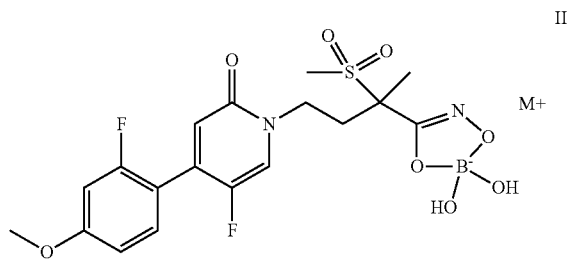

II wherein M$^+$ is a pharmaceutically acceptable monovalent cation.

A first embodiment of a third aspect of the present invention is the dimeric boronate compound of Formula III

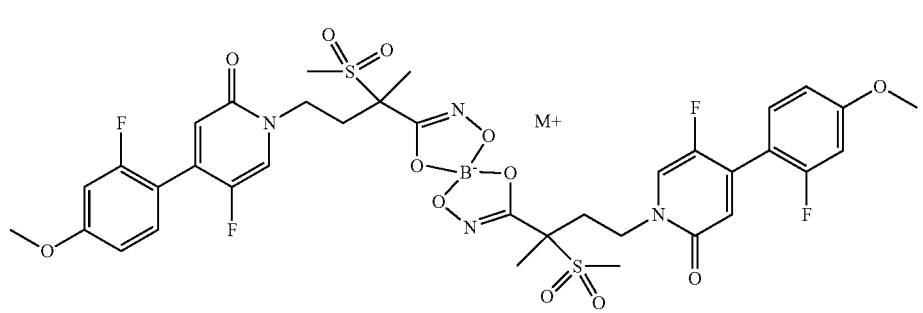

III wherein M⁺ is a pharmaceutically acceptable monovalent cation.

The compounds of Formulae I, II and III once administered to a patient in need thereof exhibit antibacterial activity, especially against Gram-negative organisms. These compounds may be used to treat bacterial infections in mammals, especially humans. The compounds may also be used for veterinary applications, such as treating infections in livestock and companion animals.

The compounds of Formulae I, II and III are useful for treating a variety of infections; especially Gram-negative infections including nosocomial pneumonia, urinary tract infections, systemic infections (bacteremia and sepsis), skin and soft tissue infections, surgical infections, intraabdominal infections, lung infections (including those in patients with cystic fibrosis), *Helicobacter pylori* (and relief of associated gastric complications such as peptic ulcer disease, gastric carcinogenesis, etc.), endocarditis, diabetic foot infections, osteomyelitis, and central nervous system infections.

In order to simplify administration, the compounds will typically be admixed with at least one excipient and formulated into a pharmaceutical dosage form. Examples of such dosage forms include tablets, capsules, solutions/suspensions for injection, aerosols for inhalation, cream/ointments for topical, otic or ophthalmic use, and solutions/suspensions for oral ingestion. The instant compounds possess enhanced aqueous solubility compared to the parent hydroxamic acid compound from which they are derived and therefore the instant compounds can advantageously be employed in injectable dosage forms.

DETAILED DESCRIPTION OF THE INVENTION

The headings within this document are only being utilized to expedite its review by the reader. They should not be construed as limiting the invention or claims in any manner.

The compounds of the present invention are prodrugs of their parent compound 4-[5-fluoro-4-(2-fluoro-4-methoxyphenyl)-2-oxopyridin-1(2H)-yl]-N-hydroxy-2-methyl-2-(methylsulfonyl)butanamide and of their preferred parent compound (2R)-4-[5-fluoro-4-(2-fluoro-4-methoxyphenyl)-2-oxopyridin-1(2H)-yl]-N-hydroxy-2-methyl-2-(methylsulfonyl) butanamide.

A second embodiment of the first aspect of the present invention is the compound of the first embodiment of the first aspect of Formula Ia

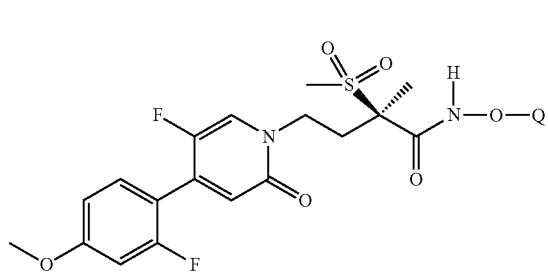

Ia which is the (R) enantiomer of the compound of Formula I and wherein Q is a group as described above for Formula I.

A third embodiment of the first aspect of the present invention is the compound of the second embodiment of the first aspect in which the group Q is —P(O)(OH)$_2$ and can be represented by Formula Ib below:

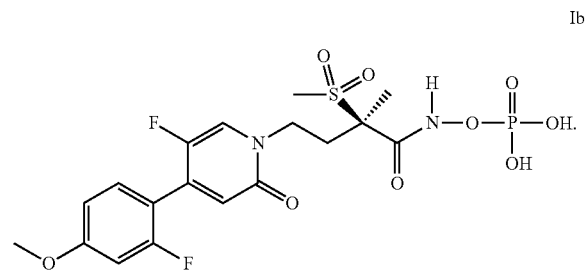 [SMILES: COc1ccc(-c2cc(=O)n(CC[C@](C)(C(=O)NOP(=O)(O)O)S(C)(=O)=O)cc2F)c(F)c1]

Ib

A fourth embodiment of the first aspect of the present invention is the compound of the second embodiment of the first aspect in which group Q is —P(O)(OH)(O⁻M⁺) and M⁺ is a pharmaceutically acceptable monovalent cation and can be represented by Formula Ic below:

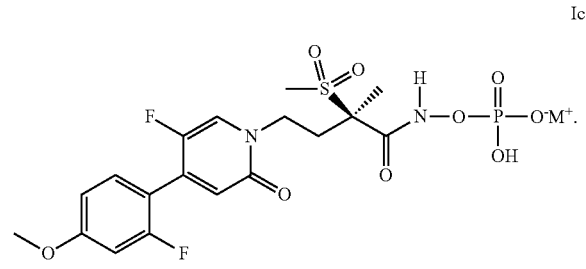

Ic

A fifth embodiment of the first aspect of the present invention is the compound of the second embodiment of the first aspect in which group Q is —P(O)(O-M⁺)(O-M⁺) and each M⁺ is a pharmaceutically acceptable monovalent cation and can be represented by Formula Id below:

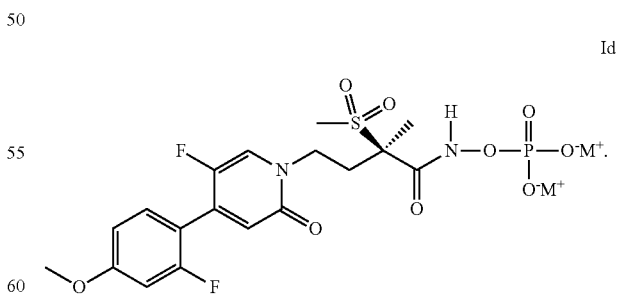

Id

A sixth embodiment of the first aspect of the present invention is the compound of the second embodiment of the first aspect in which group Q is —P(O)(O⁻)$_2$M²⁺ and each M²⁺ is a pharmaceutically acceptable divalent cation and can be represented by Formula Ie below:

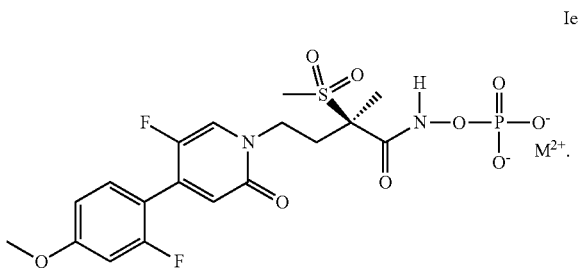

A seventh embodiment of the first aspect of the present invention is the compound of the fourth or fifth embodiments of the first aspect wherein $M^+$ at each occurrence is independently selected from the group consisting of $Li^+$, $K^+$ and $Na^+$.

An eighth embodiment of the first aspect of the present invention is the compound of the fourth or fifth embodiments of the first aspect wherein $M^+$ at each occurrence is a pharmaceutically acceptable monovalent cation independently selected from ammonium, $(C_1-C_{12}alkyl)ammonium$, $(C_1-C_{12}alkyl)_2ammonium$, $(C_1-C_{12}alkyl)_3$ ammonium, $(C_1-C_{12}alkyl)_4ammonium$, $(C_3-C_6cloalkyl)ammonium$, $(C_3-C_6cloalkyl)_2$ ammonium, $(C_3-C_6cloalkyl)_3ammonium$, $(C_3-C_6cloalkyl)_4ammonium$, pyrrolidinium, piperidinium and pyridinium; wherein each of the $(C_1-C_{12}alkyl)$ or $(C_3-C_6cycloalkyl)$ moieties are optionally substituted with one to three hydroxy or halo.

A ninth embodiment of the first aspect of the present invention is the compound of the fourth or fifth embodiments of the first aspect wherein $M^+$ at each occurrence is a pharmaceutically acceptable monovalent cation independently selected from the group consisting of glycinium, alaninium, β-alaninium, valinium, lysinium, isoleucinium, leucinium, methioninium, threoninium, asparaginium, glutaminium, histidinium, argininium, ornithinium, tryptophanium, prolinium, glutaminium, cysteinium, phenylalaninium, tyrosinium and serinium.

A tenth embodiment of the first aspect of the present invention is a compound of the fourth or fifth embodiments of the first aspect of the formula

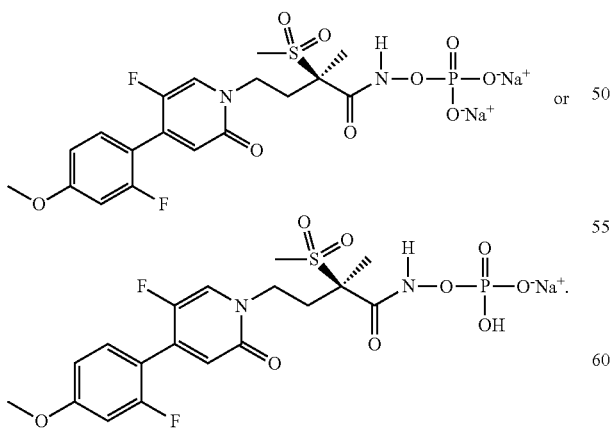

An eleventh embodiment of the first aspect of the present invention is the compound of the fourth or fifth embodiments of the first aspect of the formula

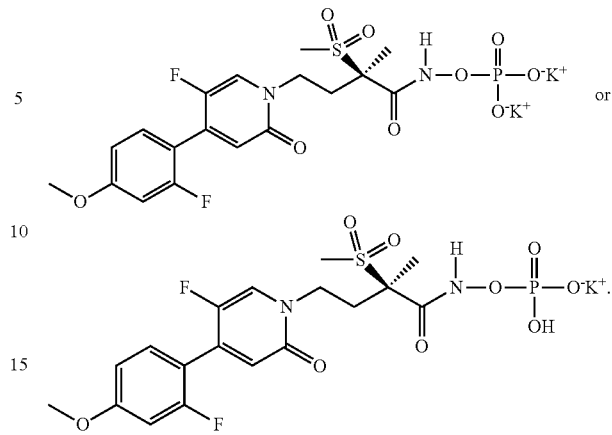

A twelfth embodiment of the first aspect of the present invention is a compound of the fourth or fifth embodiments of the first aspect of the formula

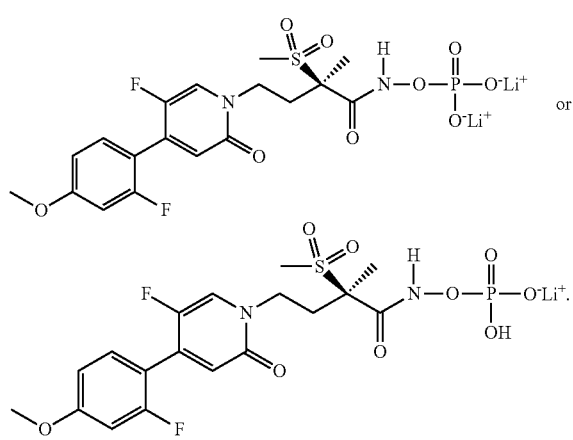

A thirteenth embodiment of the first aspect of the present invention is a compound of the fourth or fifth embodiments of the first aspect of the formula

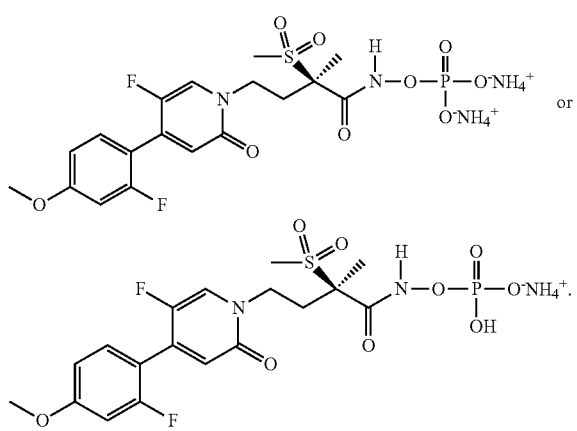

A fourteenth embodiment of the first aspect of the present invention is the compound of the fourth or fifth embodiments of the first aspect of the formula

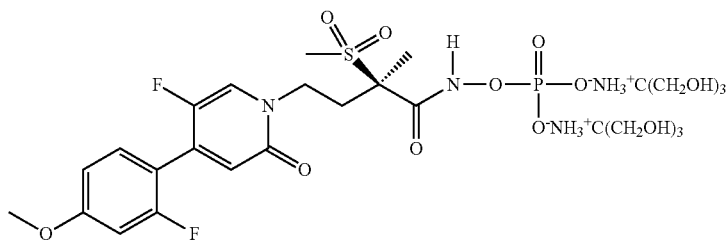

or

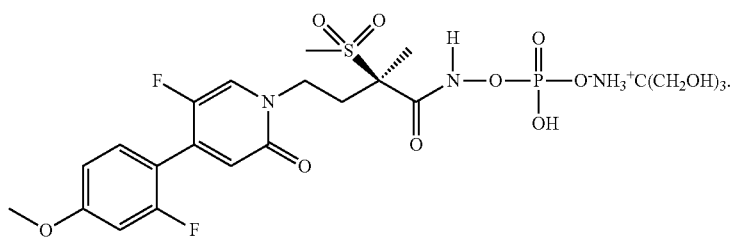

A fifteenth embodiment of the first aspect of the present invention is a compound of the fourth or fifth embodiments of the first aspect of the formula

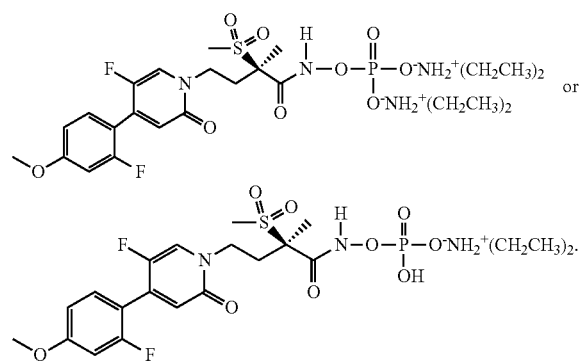

A sixteenth embodiment of the first aspect of the present invention is a compound according to the sixth embodiment of the first aspect wherein $M^{2+}$ is selected from the group consisting of $Ca^{2+}$, $Mg^{2+}$ and $Zn^{2+}$.

A second embodiment of a second aspect of the present invention is the compound according to the first embodiment of the second aspect of the formula IIa

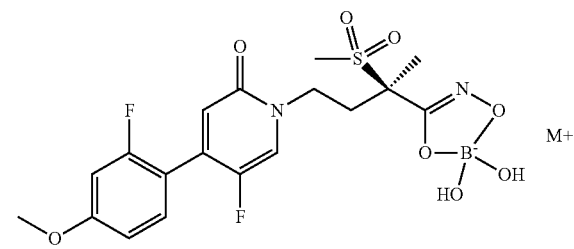

IIa wherein $M^+$ is a pharmaceutically acceptable monovalent cation.

A third embodiment of a second aspect of the present invention is the compound according to the second embodiment of the second aspect wherein $M^+$ is selected from the group consisting of $Li^+$, $K^+$ and $Na^+$.

A fourth embodiment of a second aspect of the present invention is the compound according to the second embodiment of the second aspect wherein $M^+$ is selected from ammonium, $(C_1-C_{12}$alkyl)ammonium, $(C_1-C_{12}$alkyl)$_2$ammonium, $(C_1-C_{12}$alkyl)$_3$ ammonium, $(C_1-C_{12}$alkyl)$_4$ammonium, $(C_3-C_6$cycloalkyl)ammonium, $(C_3-C_6$cycloalkyl)$_2$ ammonium, $(C_3-C_{12}$cloalkyl)$_3$ammonium, $(C_3-C_{12}$cloalkyl)$_4$ammonium, pyrrolidinium, piperidinium and pyridinium; wherein each of the $(C_1-C_{12}$alkyl) or $(C_3-C_{12}$cloalkyl) moieties are optionally substituted with one to three hydroxy or halo.

A fifth embodiment of a second aspect of the present invention is the compound according to second embodiment of the second aspect wherein $M^+$ is selected from the group consisting of glycinium, alaninium, β-alaninium, valinium, lysinium, isoleucinium, leucinium, methioninium, threoninium, asparaginium, glutaminium, histidinium, argininium, ornithinium, tryptophanium, prolinium, glutaminium, cysteinium, phenylalaninium, tyrosinium and serinium.

A second embodiment of a third aspect of the present invention is a compound of the first embodiment of the third aspect which is the dimeric boronate compound of Formula IIIa

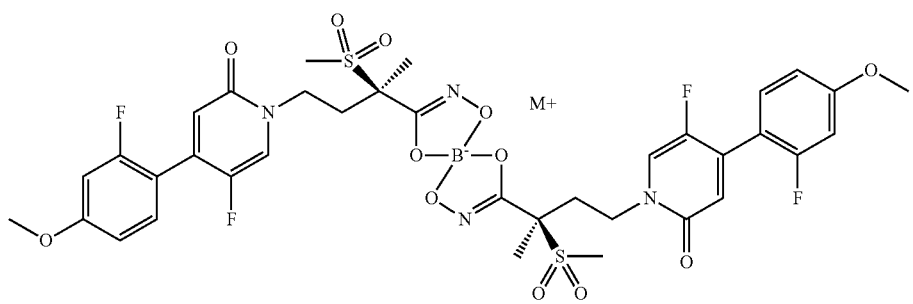

IIIa wherein M⁺ is a pharmaceutically acceptable monovalent cation.

A third embodiment of a third aspect of the present invention is a compound of the second embodiment of the third aspect wherein M⁺ is selected from the group consisting of Li⁺, K⁺ and Na⁺.

A fourth embodiment of a third aspect of the present invention is a compound of the second embodiment of the third aspect wherein M⁺ is selected from ammonium, ($C_1$-$C_{12}$alkyl)ammonium, ($C_1$-$C_{12}$alkyl)$_2$ammonium, ($C_1$-$C_{12}$alkyl)$_3$ammonium, ($C_1$-$C_{12}$alkyl)$_4$ammonium, ($C_3$-$C_6$cycloalkyl)ammonium, ($C_3$-$C_6$cycloalkyl)$_2$ammonium, ($C_3$-$C_6$cycloalkyl)$_3$ammonium, ($C_3$-$C_6$cycloalkyl)$_4$ammonium, pyrrolidinium, piperidinium and pyridinium; wherein each of the ($C_1$-$C_{12}$alkyl) or ($C_3$-$C_{12}$cloalkyl) moieties are optionally substituted with one to three hydroxy or halo.

A fifth embodiment of a third aspect of the present invention is a compound of the second embodiment of the third aspect wherein M⁺ is selected from the group consisting of glycinium, alaninium, β-alaninium, valinium, lysinium, isoleucinium, leucinium, methioninium, threoninium, asparaginium, glutaminium, histidinium, argininium, ornithinium, tryptophanium, prolinium, glutaminium, cysteinium, phenylalaninium, tyrosinium and serinium.

A first embodiment of a fourth aspect of the present invention is a pharmaceutical composition comprising a compound according to any one of the embodiments of the first through third aspects of the invention in admixture with at least one pharmaceutically acceptable excipient.

A first embodiment of a fifth aspect of the present invention is a method for a treating a Gram-negative bacterial infection in a patient, the method comprising administering a therapeutically effective amount of a compound according to any one of the embodiments of the first through third aspects of the invention to a patient in need thereof.

A second embodiment of a fifth aspect of the present invention is the method of the first embodiment of the fifth aspect wherein the Gram-negative bacterial infection is caused by a Gram-negative bacteria selected from the group consisting of *Acinetobacter baumannii, Acinetobacter* spp., *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia,* and *Pseudomonas aeruginosa.*

A third embodiment of a fifth aspect of the present invention is the method of the first embodiment of the fifth aspect wherein the Gram-negative bacterial infection is selected from the group consisting of nosocomial pneumonia, urinary tract infection, bacteremia, sepsis, skin infection, soft-tissue infection, intraabdominal infection, lung infection, endocarditis, diabetic foot infection, osteomyelitis and central nervous system infection.

A first embodiment of a sixth aspect of the present invention is the use of a compound according to any one of the embodiments of the first through third aspects of the invention for the treatment of a Gram-negative bacterial infection.

A second embodiment of a sixth aspect of the present invention is the use of the first embodiment of the sixth aspect wherein the Gram-negative bacterial infection is caused by a Gram-negative bacteria selected from the group consisting of *Acinetobacter baumannii, Acinetobacter* spp., *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia,* and *Pseudomonas aeruginosa.*

A third embodiment of a sixth aspect of the present invention is the use of the first embodiment of the sixth aspect wherein the Gram-negative bacterial infection is selected from the group consisting of nosocomial pneumonia, urinary tract infection, bacteremia, sepsis, skin infection, soft-tissue infection, intraabdominal infection, lung infection, endocarditis, diabetic foot infection, osteomyelitis and central nervous system infection.

Definitions and Exemplification

As used throughout this application, including the claims, the following terms have the meanings defined below, unless specifically indicated otherwise. The plural and singular should be treated as interchangeable, other than the indication of number:

a. "prodrug" refers to compounds which are drug precursors which, following administration and absorption, release the drug in vivo via some metabolic, catabolic or chemical process.

b. "parent compound" refers to the biologically active entity that is released via enzymatic action of a metabolic or catabolic process, or via a chemical process following administration of the prodrug.

c. "therapeutically effective amount" refers to an amount of a compound of the invention (i.e. a compound of Formulae I, II or III) that, when administered to a patient, provides the desired effect; i.e., lessening in the severity of the symptoms associated with a bacterial infection, decreasing the number of bacteria in the affected tissue, and/or preventing bacteria in the affected tissue from increasing in number (localized or systemic).

d. "patient" refers to warm blooded animals such as for example, livestock, guinea pigs, mice, rats, gerbils, cats, rabbits, dogs, monkeys, chimpanzees, and humans.

e. "treat" refers to the ability of the compounds to relieve, alleviate or slow the progression of the patient's bacterial infection (or condition) or any tissue damage associated with the disease.
f. "pharmaceutically acceptable" indicates that the substance or composition must be compatible chemically and/or toxicologically, with the other ingredients comprising a formulation, and/or the mammal being treated therewith.
g. "isomer" means "stereoisomer" and "geometric isomer" as defined below.
h. "stereoisomer" means compounds that possess one or more chiral centers and each center may exist in the R or S configuration. Stereoisomers include all diastereomeric, enantiomeric and epimeric forms as well as racemates and mixtures thereof.
i. Compounds of "Formula I", "formula I", "formula (I)", and "compounds of the invention" are being used interchangeably throughout the application and should be treated as synonyms. Like wise with respect to compounds of "Formula II", "formula II" and "formula (II)" as well as "Formula III", "formula III" and "formula (III)".
j. The terms "pyridone" and "pyridinone" have been used interchangeably within this application. No difference or distinction is meant, unless otherwise noted. One skilled in the art will readily understand this.

The phrase "monovalent cation", defined by $M^+$ herein, includes ammonium ($NH_4$), mono-, di-, tri- and tetra-($C_1$-$C_{12}$alkyl) ammonium (i.e. ($C_1$-$C_{12}$alkyl)$NH_{3+}$, ($C_1$-$C_{12}$alkyl)$_2NH_{2+}$, ($C_1$-$C_{12}$alkyl)$_3NH^+$, and ($C_1$-$C_{12}$alkyl)$_4N^+$) wherein the alkyl group(s) may be substituted as specified, mono-, di-, tri- and tetra-($C_3$-$C_{12}$cloalkyl)ammonium (i.e. ($C_3$-$C_6$cycloalkyl)$NH_{3+}$, ($C_3$-$C_6$cycloalkyl)$_2NH_{2+}$, ($C_3$-$C_6$cycloalkyl)$_3NH^+$, and ($C_3$-$C_6$cycloalkyl)$_4N^+$), alkali metal ions such as sodium, lithium and potassium ions, ions of organic amines such as pyrrolidine, piperidine or pyridine and ions of amino acids such as ions of glycine, alanine, β-alanine, valine, lysine, isoleucine, leucine, methionine, threonine, asparagine, glutamine, histidine, arginine, ornithine, tryptophane, proline, glutamine, cysteine, phenylalanine, tyrosine and serine. When the organic amine or amino acid is in its protonated form this can be denoted by the use of the suffix "ium". For example, protonated pyrrolidine is pyrrolidinium, protonated piperidine is piperidinium, protonated pyridine is pyridinium and protonated glycine is glycinium.

The term "alkyl" refers to a linear or branched-chain saturated hydrocarbyl substituent (i.e., a substituent obtained from a hydrocarbon by removal of a hydrogen); in one embodiment containing from one to twelve carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl, heptyl, octyl, nonyl, decyl, undecyl, dodecyl and the like.

The term "cycloalkyl" refers to a carbocyclic substituent obtained by removing a hydrogen from a saturated carbocyclic molecule, for example one having three to six carbon atoms. The term "$C_{3-6}$cycloalkyl" means a radical of a three to six membered ring which includes the groups cyclopropyl, cyclobutyl, cyclopentyl and cyclohexyl.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_{12}$-alkyl" or "$C_{1-12}$ alkyl" refers to an alkyl substituent containing from 1 to 12 carbon atoms and "$C_1$-$C_6$-alkyl" or "$C_{1-6}$ alkyl" refers to an alkyl substituent containing from 1 to 6 carbon atoms. Illustrating further, $C_3$-$C_6$cycloalkyl or $C_{3-6}$-cycloalkyl refers to saturated cycloalkyl group containing from 3 to 6 carbon ring atoms.

The invention relates to base addition salts of the compounds of the invention. The chemical bases that may be used as reagents to prepare these pharmaceutically acceptable base salts are those that form non-toxic base salts with such compounds. Such non-toxic base salts include, but are not limited to those derived from such pharmacologically acceptable cations ($M^+$ or $M^{2+}$) such as alkali metal cations (e.g., lithium, potassium and sodium) and alkaline earth metal cations (e.g., calcium, magnesium and zinc), ammonium, alkylamine, dialkylamine, trialkylamine, tetrakylammonium, pyridinium or water-soluble amine addition salts such as N-methylglucamine-(meglumine), and the lower alkanolammonium and other base salts of pharmaceutically acceptable organic amines such as piperidine, N-methylpiperidine, morpholine, N-methylmorpholine, amino acids, and other amines which have been used to form salts of carboxylic acids and phosphoric acids.

Suitable base salts are formed from bases which form non-toxic salts. Non-limiting examples of suitable base salts include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see *Handbook of Pharmaceutical Salts: Properties, Selection, and Use* by Stahl and Wermuth (Wiley-VCH, 2002). In addition to the methods described herein, methods for making pharmaceutically acceptable salts of phosphates and boronates are known to one of skill in the art.

The compounds of Formula I wherein Q is $P(O)(OH)(O^-M^+)$, $—P(O)(O^-M^+)_2$ or $—P(O)(O^-)_2M^{2+}$ can be prepared in a routine manner by admixture of a Formula I compound wherein Q is $—P(O)(OH)_2$ with the appropriate selected base, preferably by contact in solution employing an an excess of commonly used solvent inert solvents such as water, ether, acetonitrile, dioxane, methylene chloride, isopropanol, methanol, ethanol and ethyl acetate. The compounds of Formula I wherein Q is $P(O)(OH)(O-M^+)$, $—P(O)(O^-M^+)_2$ or $—P(O)(O^-)_2M^{2+}$ can also be prepared by metathesis or by treatment with an ion exchange resin under conditions in which a monovalent cation, $M^+$, or divalent cation, $M^{2+}$, in a compound of Formula I is replaced by another monovalent cation, $M^+$, or divalent cation, $M^{2+}$, as appropriate, under conditions which allow for separation of the desired species, such as by precipitation from solution or extraction into a solvent, or elution from or retention on an ion exchange resin. Likewise, the compounds of Formulae II or III can also be prepared by metathesis or by treatment with an ion exchange resin under conditions in which a monovalent cation, $M^+$, in a compound of Formulae II or III is replaced by another monovalent cation, $M^+$, under conditions which allow for separation of the desired species, such as by precipitation from solution or extraction into a solvent, or elution from or retention on an ion exchange resin.

The compounds of the Formula I, II and III possess one or two asymmetric center(s), thus existing as two or more stereoisomeric forms. The present invention includes all the individual stereoisomers of the compounds of Formula I, II and III and mixtures thereof. Individual enantiomers can be obtained by chiral separation or using the relevant enantiomer in the synthesis. For example, the individual (R) and (S) enantiomers of the compound of Formula I can be obtained by chiral separation from an enantiomeric mixture or they can be prepared individually using a chiral synthetic method. A preferred embodiment is the compound of Formula Ia in which the compound has the (R) stereochemistry at the chiral carbon center. Similarly, the compounds of Formulae II and III also have asymmetric centers and preferred embodiments are the compounds of Formulae IIa and IIIa which have the stereochemistry as depicted.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed within the scope of the present invention and by the claims.

The compounds of the invention act as prodrugs of 4-(5-fluoro-4-(2-fluoro-4-methoxyphenyl)-2-oxopyridin-1(2H)-yl)-N-hydroxy-2-methyl-2-(methylsulfonyl) butanamide or in a preferred embodiment of (R)-4-(5-fluoro-4-(2-fluoro-4-methoxyphenyl)-2-oxopyridin-1(2H)-yl)-N-hydroxy-2-methyl-2-(methylsulfonyl) butanamide. These compounds may have little or no pharmacological activity themselves but when administered into or onto the body, can be converted into the parent compound having the desired activity, for example, by hydrolytic cleavage of the phosphate in compounds of Formula I or of the boronate moieties in the compounds of Formulae II and III to provide the parent compound in vivo.

This invention also encompasses compounds containing protective groups. For example, certain intermediate compounds used to prepare compounds of Formulae I, II or III may contain protecting groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes isotopically-labeled compounds, which are identical to those recited in Formulae I, II or III but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as, but not limited to, $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl, respectively. Compounds of the present invention which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds of this invention can generally be prepared by carrying out the procedures disclosed in the Schemes and/or in the Examples below, by substituting a readily available isotopically-labeled reagent for a non-isotopically-labeled reagent.

All of the compounds of Formula I contain a sulfonyl moiety as depicted below:

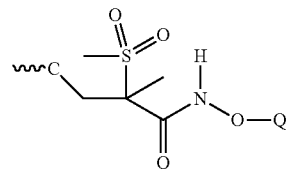

As is readily apparent to one skilled in the art, the carbon adjacent to the sulfonyl moiety is a chiral center. Therefore, the compounds can exist as the racemate, as the S-enantiomer, or as the R-enantiomer. In a further embodiment, the compounds of Formula I may be prepared and administered as the R-enantiomer (a compound of Formula Ia), as depicted below:

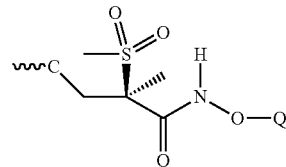

The compounds of Formulae II and III as depicted can be racemic, individual isomers or mixtures thereof whereas the compounds of Formulae IIa and IIIa have the stereochemistry as depicted for those formulae, respectively. As is readily apparent to one skilled in the art, the compounds as synthesized will rarely be present exclusively as a single enantiomer. The opposite enantiomer (i.e the S-enantiomer) may be present in minor amounts (i.e. "substantially pure"). This minor amount can be up to 10 w/w %, more typically no greater than 5 w/w %, in a further embodiment no greater than 1 w/w %, or more specifically, no greater than 0.5 w/w %.

Synthesis

The compounds of Formulae I, II and III can be prepared by a variety of methods that are analogously known in the art. The reaction schemes A and B presented below illustrate two alternative methods for preparing the intermediate compounds of Formula I' or I". Others, including modifications thereof, will be readily apparent to one skilled in the art. The compounds of Formula I' or I" can then be employed in the synthesis of compounds of Formulae I, II or III.

The synthesis of the compounds of Formula I' or I" is depicted below in Schemes A and B below. The corresponding The first step is to carry out the N-alkylation depicted in Step A. The pyridinone of structure 1 is reacted with the sulfonyl derivative of structure 2 generating the intermediate of structure 3. Structure 3 can be further derivatized to generate the compounds of Formula I. Two alternative syntheses are depicted (Option A or B), but the reader will readily note they are variations of the same synthesis. The only difference is the order in which the steps are carried out.

Initially in Option A, the halide, depicted by X, at the 4-position of the 5-fluoro-2-pyridinone of structure 3 is displaced by the desired 2-fluoro-4-methoxyphenyl moiety by reaction with 2-fluoro-4-methoxyphenyl-M¹, in which M¹ is a metal species, such as a boron derivative suitable for undergoing a typical cross-coupling such as a Suzuki-Miyaura reaction. Hydrolysis, or removal, of the ethyl protecting group (or other suitable protecting groups) in Step C affords the compound of structure 5. The terminal carboxylic acid of structure 5 is then converted to the protected hydroxamic acid derivative as depicted by structure 8. Deprotection of the protected hydroxamic acid derivative of structure 8, as depicted in Step H, affords the intermediate of Formula I'. While these reactions are well known to one skilled in the art, they are discussed in greater detail below.

Initially, in Option B of Scheme A, the ethyl protecting group (or other conventional protecting groups) is removed from the 5-fluoro-2-pyridinone of structure 3 generating the compound of structure 6 as depicted in Step E. In Step F, the terminal carboxylic acid of structure 6 is converted to the protected hydroxamic acid derivative of structure 7 via amidation conditions. In Step G, the halide function at the 4-position on the 5-fluoro-2-pyridinone moiety is then directly displaced by the desired 2-fluoro-4-methoxyphenyl moiety, by reacting 2-fluoro-4-methoxyphenyl-M¹, via a coupling reaction to afford the protected hydroxamic acid derivatives of structure 8. As before, deprotection of the protected hydroxamic acid derivatives, as depicted in Step H, affords the compounds of Formula I'.

Scheme B, depicted below, is analogous to Scheme A with the exception that the pyridinone of structure 1 is reacted with the sulfonyl derivative of structure 2' generating the intermediate of structure 3'. Structure 3' can be further derivatized to generate the compound of Formula I". Initially in Option A, the halide, depicted by X, at the 4-position of the 5-fluoro-2-pyridinone of structure 3' is displaced by the desired 2-fluoro-4-methoxyphenyl moiety by reaction with 2-fluoro-4-methoxyphenyl-M¹, in which M¹ is a metal species, such as a boron derivative suitable for undergoing a typical cross-coupling such as a Suzuki-Miyaura reaction. Hydrolysis, or removal, of the ethyl protecting group (or other suitable protecting groups) in Step C affords the compound of structure 5'. The terminal carboxylic acid of structure 5' is then converted to the protected hydroxamic acid derivative as depicted by structure 8'. Deprotection of the protected hydroxamic acid derivative of structure 8', as depicted in Step H, affords the intermediate of Formula I". While these reactions are well known to one skilled in the art, they are discussed in greater detail below.

Initially, in Option B of Scheme B, the ethyl protecting group (or other conventional protecting groups) is removed from the 5-fluoro-2-pyridinone of structure 3' generating the compound of structure 6' as depicted in Step E. In Step F, the terminal carboxylic acid of structure 6' is converted to the protected hydroxamic acid derivative of structure 7' via amidation conditions. In Step G, the halide function at the 4-position on the 5-fluoro-2-pyridinone moiety is then directly displaced by the desired 2-fluoro-4-methoxyphenyl moiety, by reacting 2-fluoro-4-methoxyphenyl-M¹, via a coupling reaction to afford the protected hydroxamic acid derivatives of structure 8'. As before, deprotection of the protected hydroxamic acid derivatives, as depicted in Step H, affords the compounds of Formula I".

SCHEME A

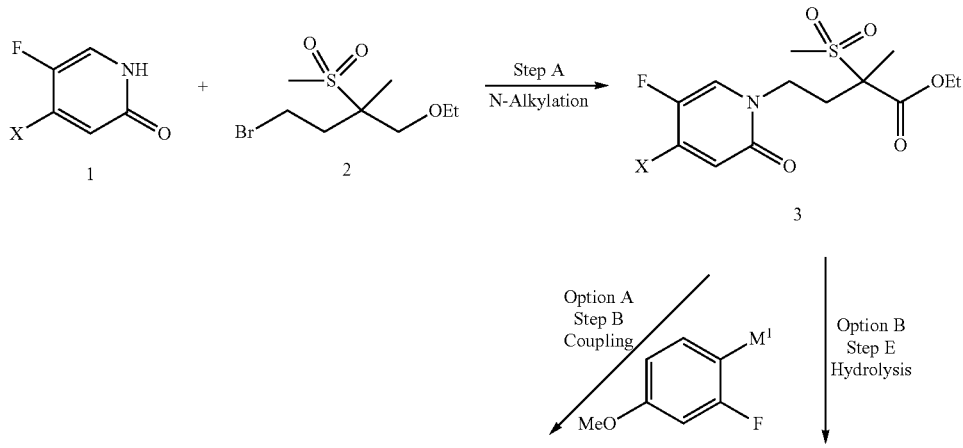

-continued
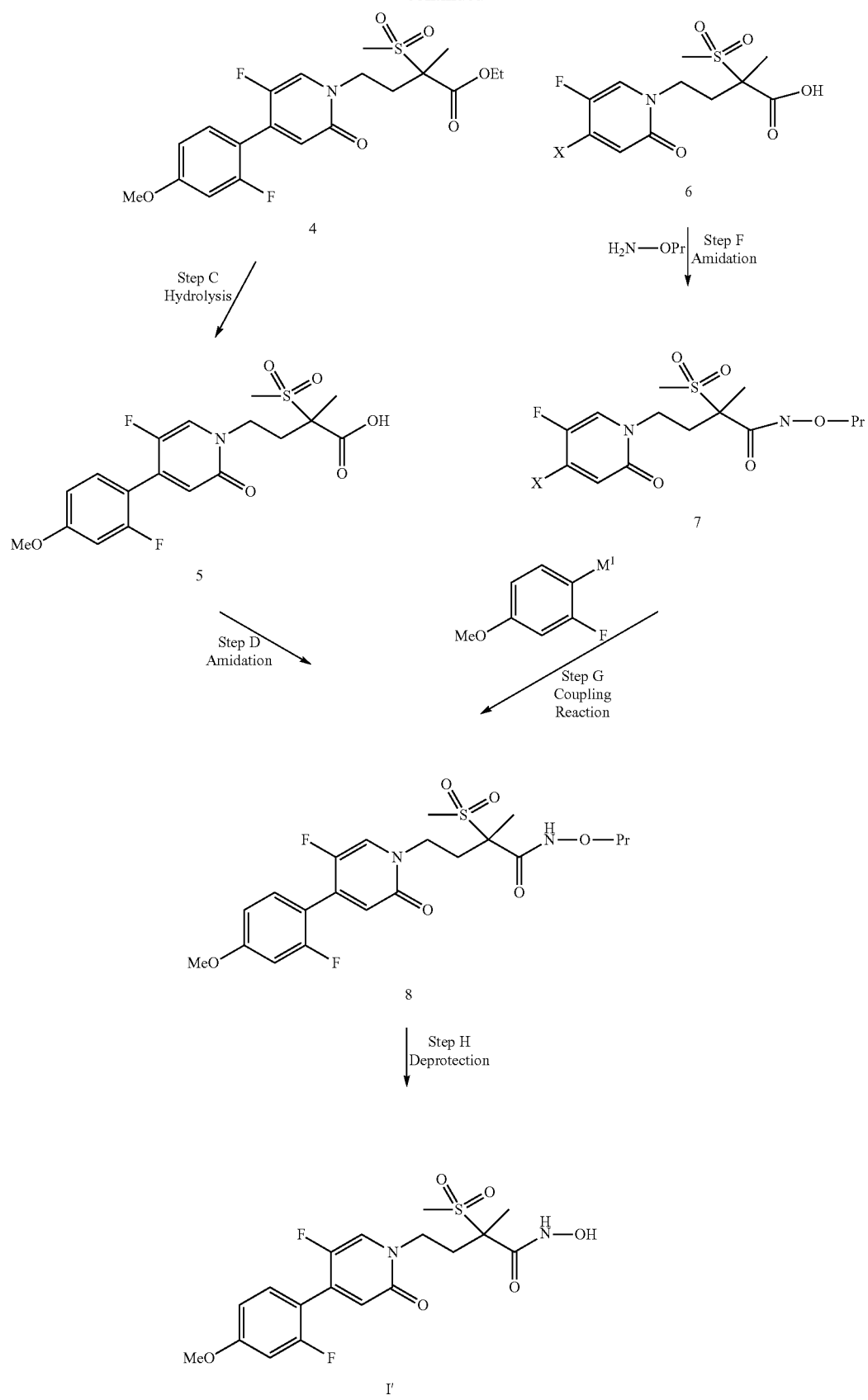

SCHEME B
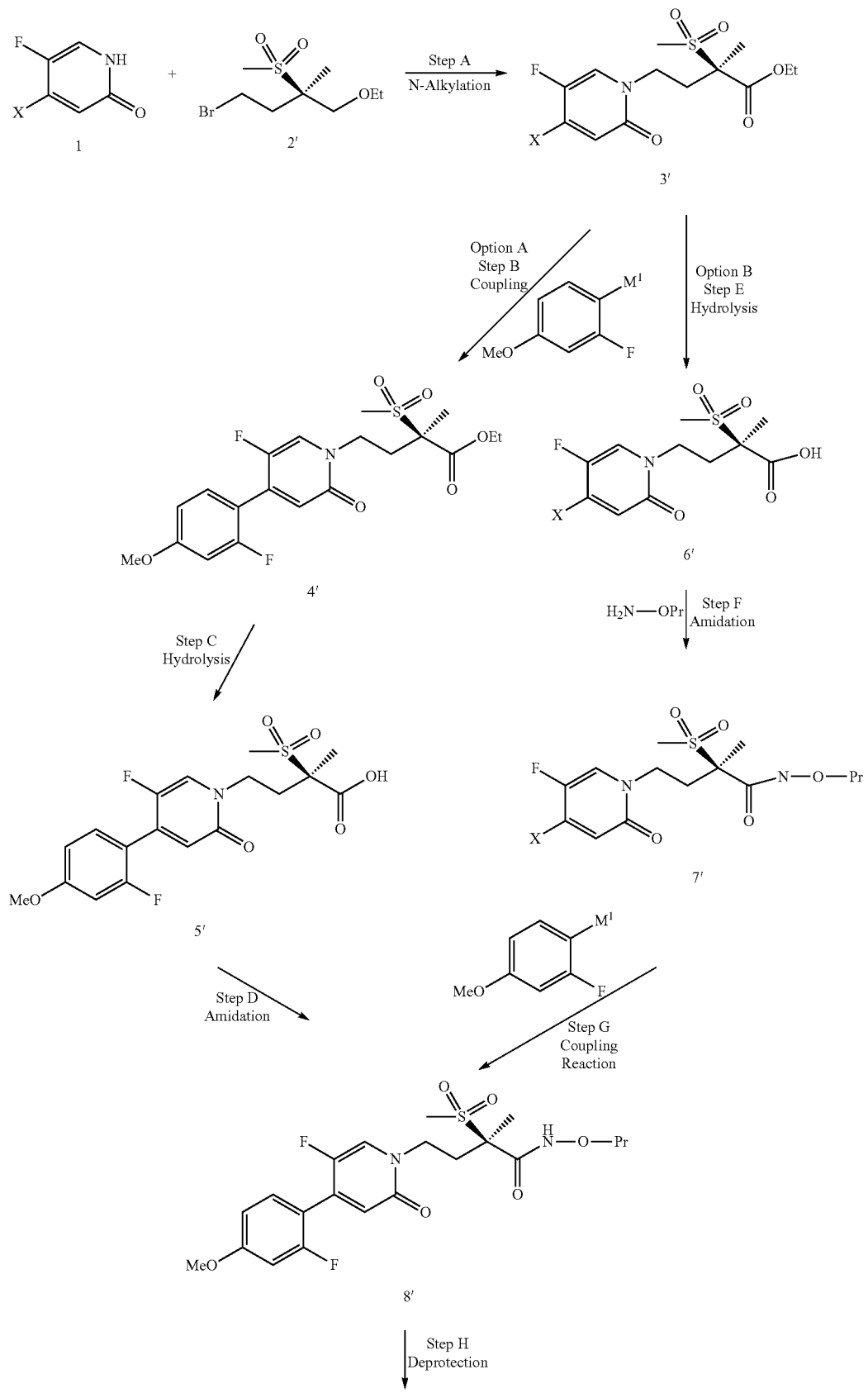

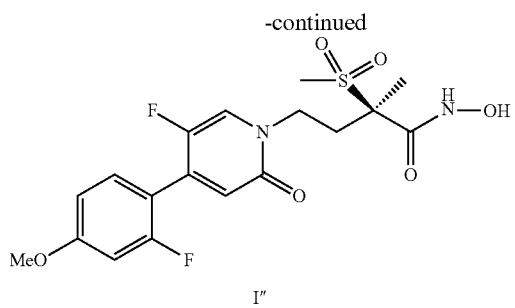

I″

The following description relates to the synthetic steps used in Schemes A and B. The N-alkylation depicted above in Step A of Scheme A and Scheme B can be carried out using techniques well known to one skilled in the art. One of the starting materials is the 5-fluoro-2-pyridinone derivative of structure 1. In this pyridinone, X is an appropriate leaving group such as a halide. Many of these pyridinone derivatives are known in the art and the remainder can be produced using synthetic techniques analogously known in the art. The reader's attention is directed to *Tet. Lett.* (2005) *Vol* 46, 7917, for a description of such techniques. Preparation 2 infra, also illustrates their preparation.

The other reactant in the N-alkylation depicted in Step A is the protected alkyl sulfonate of structure 2 or 2'. In structure 2 or 2' an ethyl protecting group is portrayed (i.e. protecting the carboxylic acid as its ethyl ester), but any standard carboxylic acid protecting group may be substituted. These alkyl sulfonates are also known in the art. The reader's attention is directed to *Journal of Organic Chemistry*, (1980) *Vol* 45, 8, 1486-1489 for a description of their preparation. Preparation 1 infra, also illustrates their preparation.

The N-alkylation can be carried out as is known in the art. Typically, equivalent amounts of the compounds of structure 1 and 2 or 2' are contacted in a mixture of aprotic and protic solvents, such as tetrahydrofuran and t-butanol, in the presence of a base such as potassium carbonate, cesium carbonate, sodium carbonate, sodium hydride, etc. A transfer agent, such as tetrabutyl ammonium bromide, can be utilized, if desired. The reactants are typically heated and the reaction is allowed to proceed to completion. The desired product of structure 3 or 3' can be isolated by methods known in the art. If desired, the product of structure 3 or 3' can be purified, or alternatively the crude can be used in the next step of the reaction. Preparation 2 infra, illustrates such an N-alkylation.

Scheme A illustrates how to incorporate the hydroxamic acid moiety into the molecules. Initially, the protecting group is removed from the carboxylic acid, thereby generating the intermediate of structure 5 or 5' and 6 or 6', as depicted in Step C (Option A) and Step E (Option B) respectively. The manner in which this is accomplished will vary with the identity of the actual protecting group and is well known to those skilled in the art. The reader's attention is directed to McOmie or Greene supra, for a discussion of potential protecting groups and methods for their removal. Preparation 2 infra describes how to remove an ethyl moiety as depicted in Schemes A and B.

In Steps F and D, the hydroxamic acid moiety as depicted, is incorporated into the molecule. A protected hydroxylamine source may be used followed by a subsequent deprotection reaction (alternatively, hydroxylamine may be directly incorporated to eliminate the deprotection steps). In either case the hydroxamic acid is incorporated into the molecule using standard amidation reactions. For example, the compound of structure 5 or 5' (Option A) or 6 or 6' (Option B) may be contacted with an excess of oxalyl chloride, in an aprotic solvent such as dichloromethane for a sufficient period of time to allow the formation of the corresponding acid chloride, followed by the addition of an excess of either hydroxylamine or protected hydroxylamine. The reaction is then allowed to proceed to completion and the protected intermediates of structure 7 or 7' (Option B) or 8 or 8' (Option A) is isolated from the reaction medium and purified as is known in the art. As mentioned above, any deprotection may be carried out as is known in the art (See Greene or McOmie supra). Alternatively, the amide can be formed using the amide coupling reagent, 1,1'-carbonyldiimidazole (CDI), 2-chloro-4,6-dimethoxy-1,3,5-triazine (CDMT), or 1-ethyl-3-(3-dimethylaminopropyl)carbodiimide (EDCI), as is known in the art.

Schemes A and B also depict how to incorporate the terminal 2-fluoro-4-methoxyphenyl moiety, into the molecule. Regardless of whether Option A or Option B is chosen, a coupling reaction is ultimately carried out to attach the terminal 2-fluoro-4-methoxyphenyl moiety, to the 4-position of the pyridinone intermediate. In both Scheme A and B, the co-reactant is depicted as 2-fluoro-4-methoxyphenyl-$M^1$, where $M^1$ represents a metal (or metalloid) such as magnesium, copper, tin, boronic ester/acid, etc. at the desired point of attachment to the pyridinone intermediate of structure 3 or 3' or 7 or 7' (i.e. the other reactant).

The coupling reaction can be carried out by a variety of techniques. The Suzuki-Miyaura strategy can be used to form the carbon-carbon bond. In such a reaction $M^1$ will be represented by a boronic acid/ester. Equivalent molar amounts of the reactants will be contacted in a solvent such as tetrahydrofuran, 2-methyltetrahydrofuran, 1,4-dioxane, water, toluene, or a mixture thereof in the presence of a transition metal catalyst such as a free or resin bound palladium or nickel species, together with a base such as sodium carbonate, potassium carbonate, cesium fluoride, cesium carbonate, etc. The reaction mixture can be heated by microwave or by other conventional techniques until adequate conversion is achieved. Once complete, the desired product may be isolated and recovered from the reaction and further purified as is known in the art. Analogously, other carbon-carbon bond forming methods known in the art can be employed to carry out the coupling reaction. In such a reaction $M^1$ can be represented by an in situ generated cuprate species or a trialkyl tin moiety, such as trimethylstannyl, tributylstannyl or tri-t-butylstannyl. Equivalent molar amounts of the reactants will be contacted in a solvent such as tetrahydrofuran, 2-methyltetrahydrofuran, dimethylformamide or a mixture thereof in the presence of a transition metal catalyst such as free or resin bound palla-

SCHEME C

I'

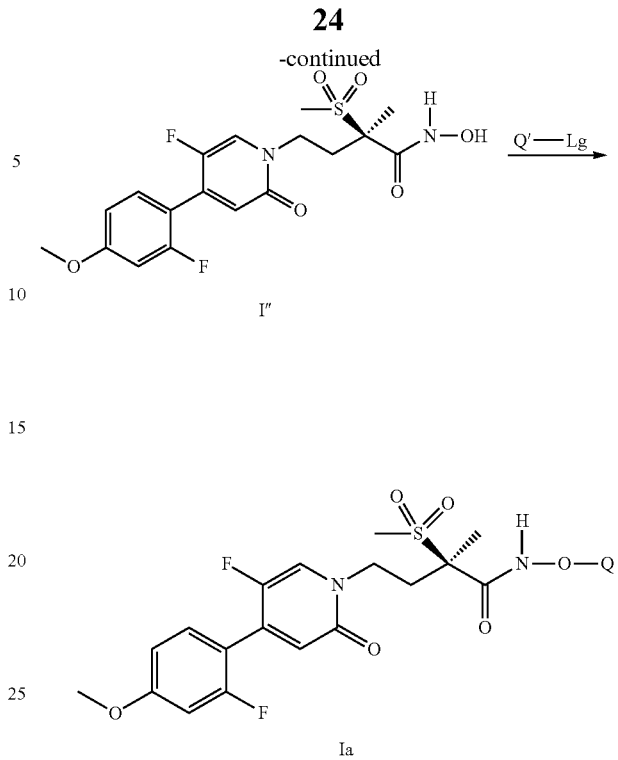

I''

Ia

I

Scheme C depicts the preparation of compounds of Formulae I and Ia from compounds I' and I'', respectively. The compound of Formula I' or I'' is reacted with an appropriate phosphate precursor compound, Q'-Lg, wherein Lg represents an appropriate leaving group and Q' represents a phosphorous containing group that can be converted to an appropriate phosphate group Q. Examples of phosphate precursor compounds Q'-Lg include phosphorous oxychloride (POCl$_3$) or a phosphoramidite reagent (PgO)$_2$P—NR'$_2$. Under appropriate reaction conditions the Q' moiety is converted into the group Q as set forth in Formula I or Ia. A more detailed description of such conversions of Q' to Q is provided below in Schemes D and E.

SCHEME D

I''

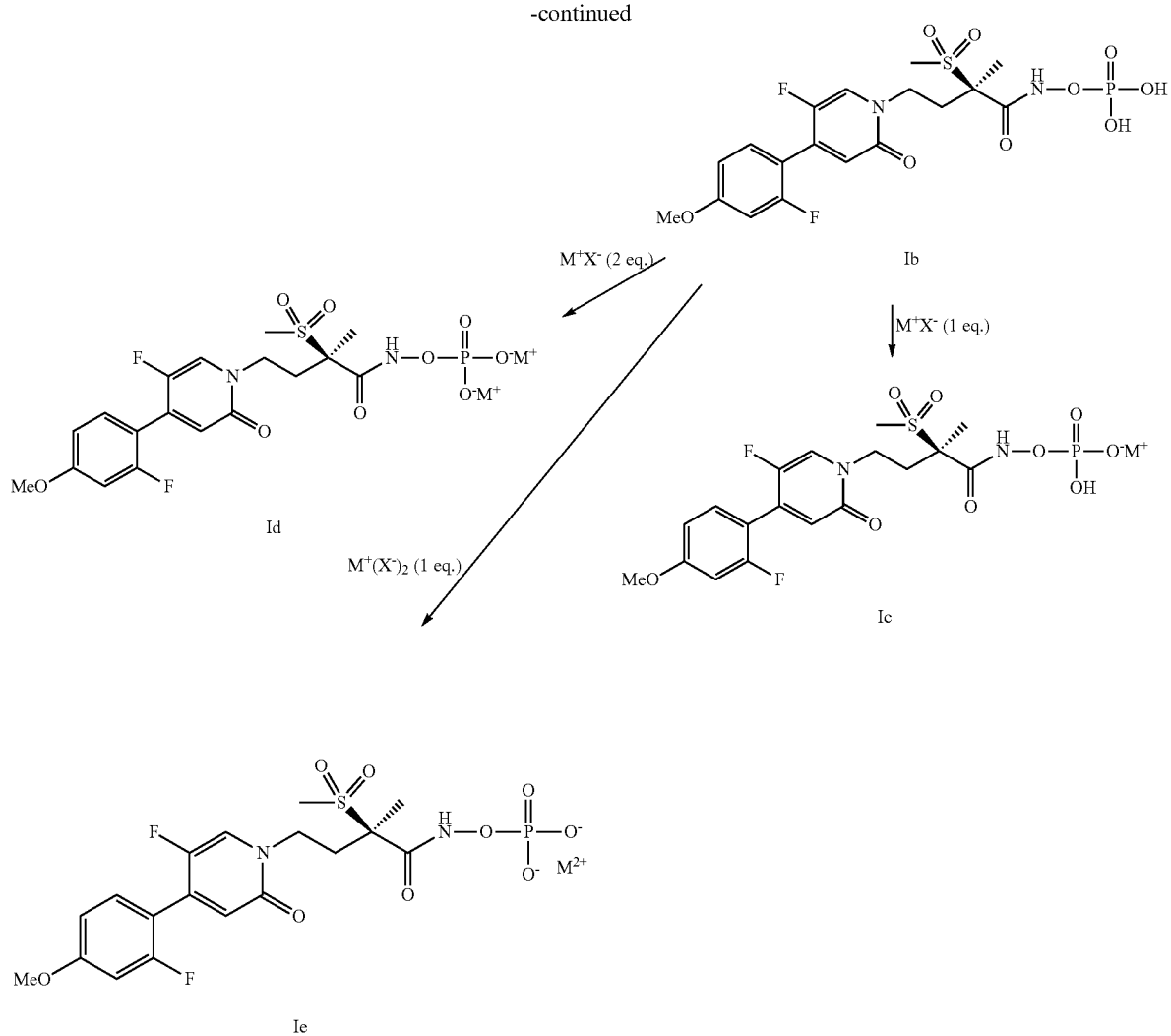

Scheme D depicts the preparation of novel phosphates within the scope of Formula I (i.e. compounds of Formulae Ib, Ic, Id and Ie). The hydroxamic acid compound of Formula I″ is dissolved in an appropriate solvent, such as acetonitrile, and treated with an appropriate base, such as N-methylmorpholine at a reduced temperature, such as 0° C. to −10° C. The resulting mixture is then reacted with phosphorous oxychloride and can then be quenched with water to provide the phosphate of Formula Ib. The compound of Formula Ib can then be reacted with an appropriate base (i.e. $M^+X^-$ or $M^{2+}(X^-)_2$ wherein $X^-$ is an anionic counterion) as shown to provide the compounds of Formulae Ic, Id or Ie. Alternatively, the compound of formula Ib could be treated with an appropriate ion exchange resin, such as a Dowex ion exchange resin, in an aqueous solution to provide a compound of formula Id.

SCHEME E

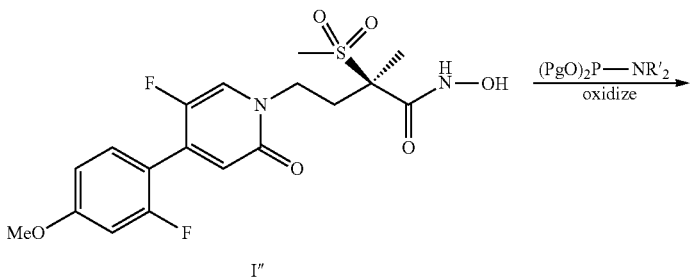

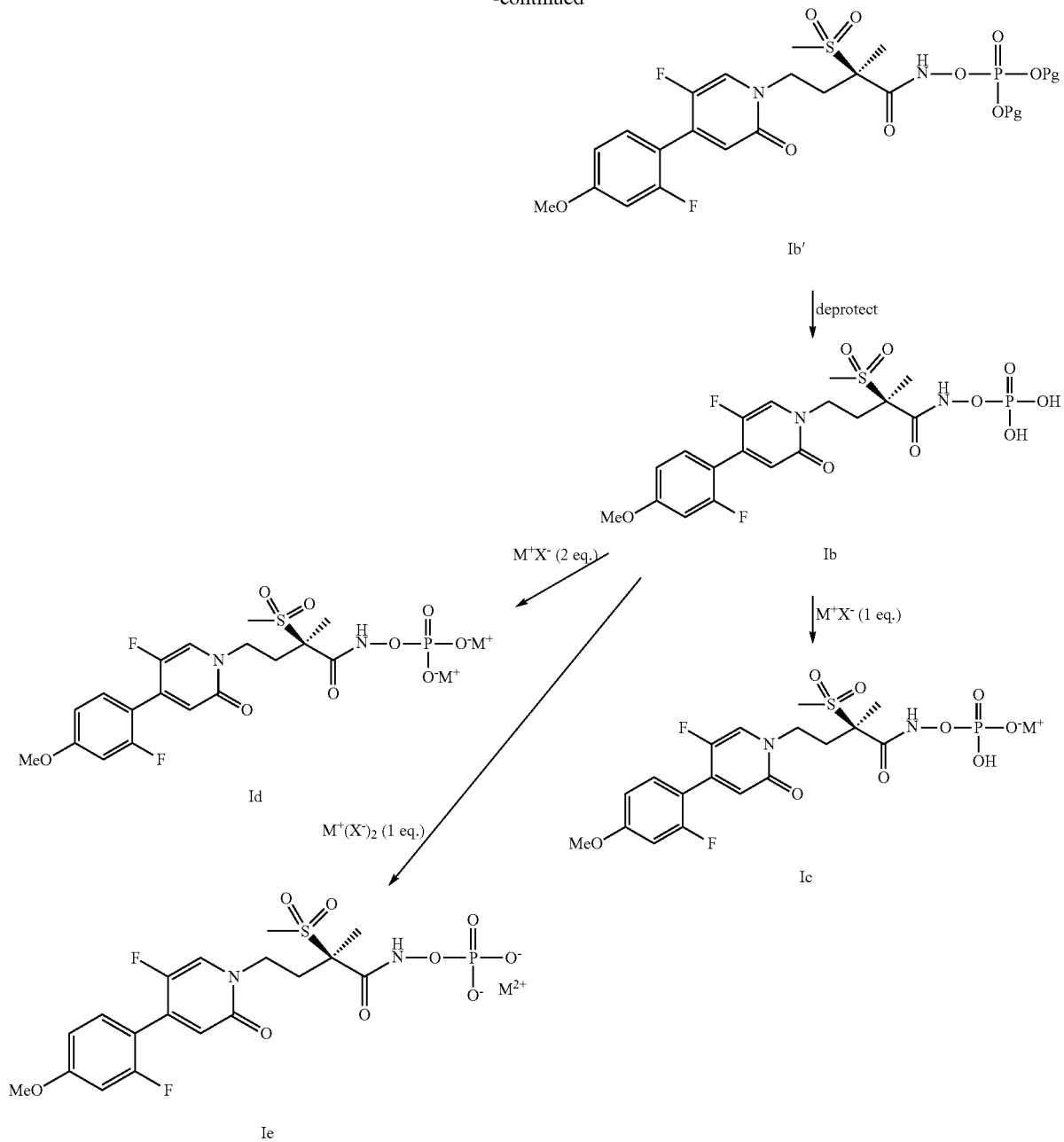

Scheme E depicts an alternative method for preparing the compounds of formulae Ib-Ie. The compound of Formula I″ is reacted with a suitable phosphoramidite reagent, $(PgO)_2P-NR'_2$, in which the group Pg represents an appropriate protecting group such as t-butyl or benzyl and the group R' represents a lower alkyl group such as ethyl or isopropyl. The reaction is typically carried out at approximately ambient temperature in an appropriate solvent such as acetonitrile, dichloromethane or a mixture thereof in the presence of an activating agent such as tetrazole for a period of one to eight hours. The reaction mixture can then be cooled and in situ oxidation carried out by treatment with an appropriate oxidizing agent such as hydrogen peroxide, t-butyl hydroperoxide or m-CPBA to provide the compound of Formula Ib'. The compound of Formula Ib' is then deprotected using standard methodology to provide the compounds of Formula Ib. For example, when Pg represents t-butyl the compound of Formula Ib' can be deprotected by treatment with a strong acid such as hydrochloric acid or trifluoroacetic acid. Alternatively, when Pg represents benzyl the compound of Formula Ib' can be deprotected by catalytic hydrogenation. The compound of Formula Ib can then be used to prepare the compounds of Formulae Ic, Id or Ie as previously described for Reaction Scheme D.

SCHEME F

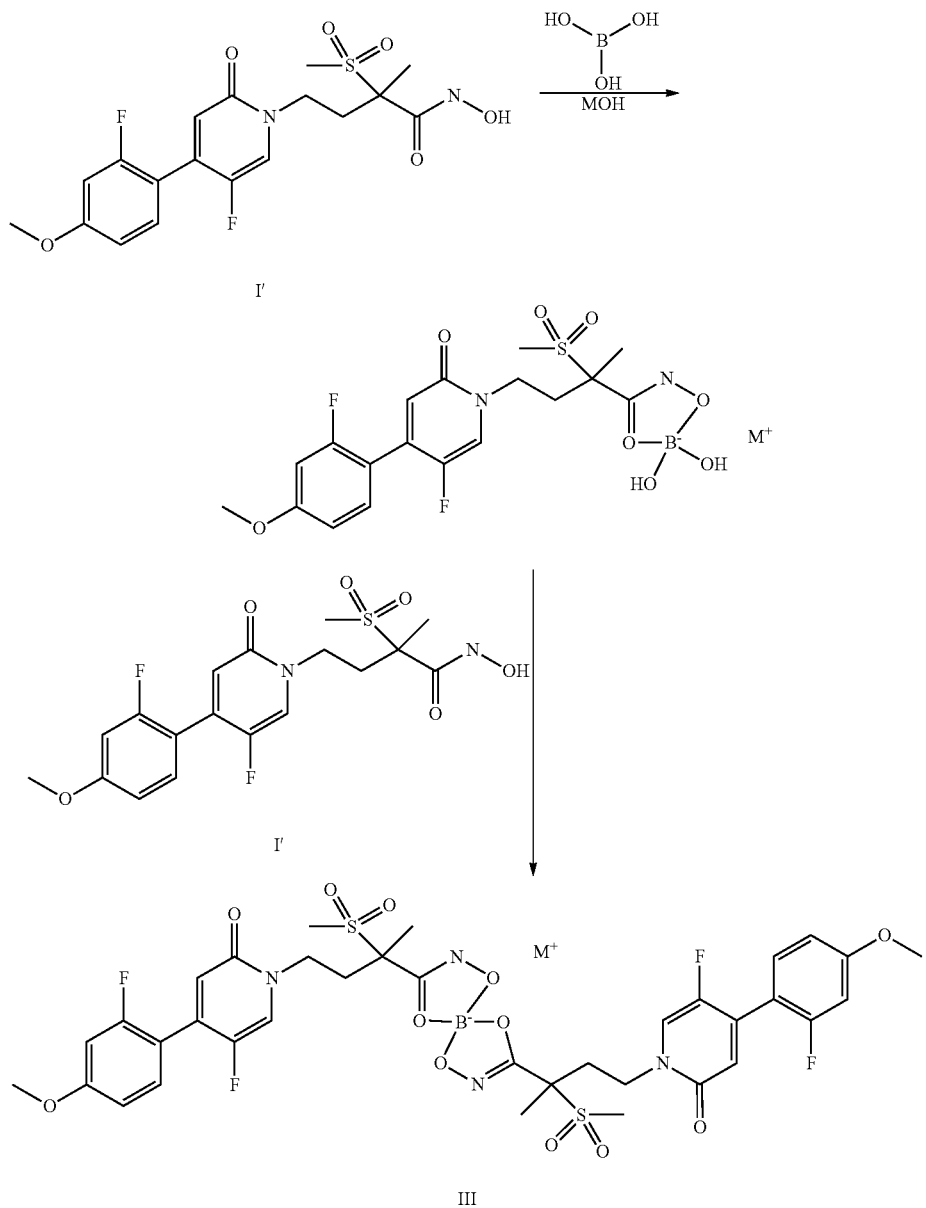

Scheme F depicts the preparation of the borate monomer and dimer compounds of Formulae II and III. One equivalent of the hydroxamic acid of Formula I' is combined with one equivalent of boric acid in water in the presence of one equivalent of an appropriate base such as sodium hydroxide, potassium hydroxide or lithium hydroxide (MOH). The mixture is stirred at ambient temperature for 30 minutes to four hours then the mixture can be either concentrated in vacuo or frozen and lyophilized to provide the monoboronate compound of Formula II. The monoboronate of Formula II can be combined with another equivalent of the compound of Formula I' and then dissolved in an appropriate solvent such as THF, with heating as necessary. The mixture can be concentrated in vacuo to provide crude boronate dimer of Formula III which may be redissolved in an appropriate solvent such as THF. To the solution can be added an appropriate solvent such as pentane to induce precipitation. The mixture can then be stirred and the product of Formula III can be collected by filtration. It is to be understood that the reaction sequence depicted in Scheme F can also be carried using the compound of Formula I" instead of Formula I' to provide the corresponding monoboronate of Formula IIa and boronate dimer of Formula IIIa.

The reaction schemes depicted above for producing the compounds of the invention are merely illustrative. As is readily apparent to one skilled in the art, they may be modified depending upon the specific compound, availability of reagents, etc.

Medical and Veterinary Uses

The compounds of Formulae I, II or III may be used for the treatment or prevention of infectious disorders, especially those caused by susceptible and multi-drug resistant (MDR) Gram-negative bacteria. Examples of such Gram-negative bacteria include *Acinetobacter baumannii, Acinetobacter* spp., *Achromobacter* spp., *Aeromonas* spp., *Bacteroides fragilis, Bordetella* spp., *Borrelia* spp., *Brucella* spp., *Campylobacter* spp., *Citrobacter diversus (koseri), Citrobacter freundii, Enterobacter aerogenes, Enterobacter cloacae, Escherichia coli, Francisella tularensis, Fusobacterium* spp., *Haemophilus influenzae* (β-lactamase positive and negative), *Helicobacter pylori, Klebsiella oxytoca, Klebsiella pneumoniae* (including those encoding extended-spectrum β-lactamases (hereinafter "ESBLs"), *Legionella pneumophila, Moraxella catarrhalis* (β-lactamase positive and negative), *Morganella morganii, Neisseria gonorrhoeae, Neisseria meningitidis, Proteus vulgaris, Porphyromonas* spp., *Prevotella* spp., Mannheimia *haemolyticus, Pasteurella* spp., *Proteus mirabilis, Providencia* spp., *Pseudomonas aeruginosa, Pseudomonas* spp., *Salmonella* spp., *Shigella* spp., *Serratia marcescens, Treponema* spp., *Burkholderia cepacia, Vibrio* spp., *Yersinia* spp., and *Stenotrophomonas mulophilia*. Examples of other gram negative organisms include members of the Enterobacteriaceae that express ESBLs; KPCs, CTX-M, metallo-β-lactamases (such as NDM-1, for example), and AmpC-type beta-lactamases that confer resistance to currently available cephalosporins, cephamycins, carbapenems, and beta-lactam/beta-lactamase inhibitor combinations.

In a more specific embodiment, the Gram-negative bacteria are selected from the group consisting of *Acinetobacter baumannii, Acinetobacter* spp., *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia, Pseudomonas aeruginosa* and members of the Enterobacteriaceae and *Pseudomonas* that express ESBLs, KPCs, CTX-M, metallo-β-lactamases, and AmpC-type beta-lactamases that confer resistance to currently available cephalosporins, cephamycins, carbapenems, and beta-lactam/beta-lactamase inhibitor combinations.

Examples of infections that may be treated with the compounds of Formulae I, II and III include nosocomial pneumonia, urinary tract infections, systemic infections (bacteremia and sepsis), skin and soft tissue infections, surgical infections, intraabdominal infections, lung infections in patients with cystic fibrosis, patients suffering from lung infections, endocarditis, diabetic foot infections, osteomyelitis, and central nervous system infections.

In addition, the compounds can be used to treat *Helicobacter pylori* infections in the GI tract of humans (and other mammals). Elimination of these bacteria is associated with improved health outcomes including fewer dyspeptic symptoms, reduced peptic ulcer recurrence and rebleeding, reduced risk of gastric cancer, etc. A more detailed discussion of eradicating *H. pylori* and its impact on gastrointestinal illness may be found on the world wide web at: informahealthcare.com, Expert Opin. Drug Saf. (2008) 7(3).

In order to exhibit this anti-infective activity, the compounds need to be administered in a therapeutically effective amount. A "therapeutically effective amount" is meant to describe a sufficient quantity of the compound to treat the infection, at a reasonable benefit/risk ratio applicable to any such medical treatment. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. As a general guideline however, the total daily dose will typically range from about 0.1 mg/kg/day to about 5000 mg/kg/day in single or in divided doses. Typically, dosages for humans will range from about 10 mg to about 3000 mg per day, in a single or multiple doses.

Any route typically used to treat infectious illnesses, including oral, parenteral, topical, rectal, transmucosal, and intestinal, can be used to administer the compounds. Parenteral administrations include injections to generate a systemic effect or injections directly into to the afflicted area. Examples of parenteral administrations are subcutaneous, intravenous, intramuscular, intradermal, intrathecal, and intraocular, intranasal, intravetricular injections or infusions techniques. Topical administrations include the treatment of areas readily accessible by local application, such as, for example, eyes, ears including external and middle ear infections, vaginal, open wound, skin including the surface skin and the underneath dermal structures, or lower intestinal tract. Transmucosal administration includes nasal aerosol or inhalation applications.

Formulations

Compounds of the invention can be formulated for administration in any way for use in human or veterinary medicine, by analogy with other bioactive agents such as antibiotics. Such methods are known in the art and are summarized below.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, ophthalmic ointments/drops and otic drops, impregnated dressings and aerosols, and may contain appropriate conventional additives such as preservatives, solvents to assist drug penetration and emollients, etc. Such topical formulations may also contain conventional carriers, such as cream or ointment bases and ethanol or oleyl alcohol for lotions. Such carriers may be present, for example, from about 1% up to about 98% of the formulation.

Tablets and capsules for oral administration may be in unit dose presentation form, and may contain conventional excipients such as binding agents, for example acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being typical. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, to about 100% by weight, of the active material, depending on the method of administration. Where the compositions comprise dosage units, each unit will contain, for example, from about 0.5-1000 mg of the active ingredient. The dosage as employed for adult human treatment will range, for example, from about 10 to 3000 mg per day, depending on the route and frequency of administration.

If desired, the compounds of the invention may be administered in combination with one or more additional antibacterial agents ("the additional active agent"). Such use of compounds of the invention in combination with an additional active agent may be for simultaneous, separate or sequential use.

The Examples and preparations provided below further illustrate and exemplify the compounds of the present invention and methods of preparing such compounds. It is to be understood that the scope of the present invention is not limited in any way by the scope of the following Examples and preparations. In the following Examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Experimental Procedures

Experiments were generally carried out under an inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wisconsin). Mass spectrometry data is reported from either liquid chromatography-mass spectrometry (LCMS) or atmospheric pressure chemical ionization (APCI). Chemical shifts for nuclear magnetic resonance (NMR) data are expressed in parts per million (ppm, δ) referenced to residual peaks from the deuterated solvents employed. Melting points are uncorrected. Low Resolution Mass Spectra (LRMS) were recorded on either a Hewlett Packard 5989@, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20-25° C.

For syntheses referencing procedures in other Examples, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

In the discussion above and in the Examples below, the following abbreviations have the following meanings. If an abbreviation is not defined, it has its generally accepted meaning.

APCI=atmospheric pressure chemical ionization
aq=aqueous
bd=broad doublet
bm=broad multiplet
bs=broad singlet
CDMT=2-chloro-4,6-dimethoxy-1,3,5-triazine
° C.=degrees celsius
cm=centimeter
d=doublet
DCM=dichloromethane
dd=doublet of doublets
ddd=doublet of doublets of doublets
DMF=dimethylformamide
DMSO=dimethyl sulfoxide
$D_2O$=deuterium oxide
dq=doublet of quartets
dt=doublet of triplets
ee=enantiomeric excess
EtOAc=ethyl acetate
g=grams
h=hours
$^1H$=proton
HCl=hydrochloric acid
HPLC=high pressure liquid chromatography
Hz=hertz
J=coupling constant
Kg=kilogram
L=liter
LCMS=liquid chromatography mass spectrometry
m=multiplet
M=molar
mCPBA=meta-chloroperbenzoic acid
μg=microgram
μL=microliter
mg=milligram
$MgSO_4$=magnesium sulfate
MHz=megahertz
min=minutes
mL=milliliter mm=millimeter
mmol=millimole
MS=mass spectrometry
m/z=mass to charge ratio
N=normality
NaOH=sodium hydroxide
NMR=nuclear magnetic resonance
ppm=parts per million
q=quartet
rt=retention time
RT=room temperature
s=singlet
t=triplet
TFA=trifluoroacetic acid
THF=tetrahydrofuran
THP=tetrahyropyranyl
TMS=tetramethylsilane
UDP=uridine 5'-diphosphate Preparation of Starting Materials Preparation 1

Synthesis of Template 1 (T1): Ethyl 4-bromo-2-methyl-2-(methylsulfonyl)butanoate and its Individual (R) and (S) Enantiomers

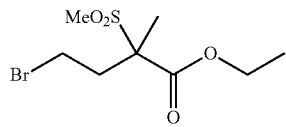

Step A) Ethyl 2-(methylsulfonyl)propanoate

Sodium methanesulfinate (103 g, 937 mmol) was combined with ethyl 2-chloropropionate (109 g, 892 mmol) in ethanol (350 mL) in a 500 mL one neck round bottom flask. The reaction was heated to 77° C. for 20 h, and then allowed to cool to room temperature. The solids were removed by filtration through celite, and the filter pad was washed with ethanol. The combined filtrates were concentrated in vacuo. The crude product was suspended in diethyl ether (250 mL), and solids were removed by filtration. The filtrate was concentrated in vacuo to afford the title compound as a pale yellow oil (51 g, 73%). $^1$H NMR (400 MHz, CHLOROFORM-d) δ ppm 1.32 (t, J=7.05 Hz, 3H) 1.67 (d, J=7.47 Hz, 3H) 3.05 (s, 3H) 3.83-3.92 (m, 1H) 4.18-4.37 (m, 2H).

Step B) Ethyl 4-bromo-2-methyl-2-(methylsulfonyl)butanoate

Sodium hydride (60% dispersion in mineral oil, 2.33 g, 58.3 mmol) was washed with hexanes (2×10 mL) in a 100 mL two neck round bottom flask under nitrogen then suspended in DMF (30 mL). The suspension was treated dropwise with ethyl 2-(methylsulfonyl)propanoate (10.0 g, 55.49 mmol) in DMF (10 mL). The mixture was stirred 30 min at RT, cooled to 0° C., and treated drop-wise with 1,2-dibromoethane (5.17 mL, 58.8 mmol). The mixture was allowed to warm to room temperature while stirring overnight. The mixture was quenched with saturated aq ammonium chloride (100 mL) and extracted with diethyl ether (4×50 mL). Combined organics were washed with 50% saturated sodium chloride (4×50 mL), dried (MgSO$_4$), and concentrated in vacuo. Crude material was purified via silica chromatography (350 g, 230-400 mesh) and an eluent of EtOAc in hexanes (10-20%) to afford the title compound as a pale yellow oil (7.9 g, 50%). $^1$H NMR (400 MHz, CHLOROFORM-d) δ ppm 1.33 (t, J=7.05 Hz, 3H) 1.64 (s, 3H) 2.49-2.59 (m, 1H) 2.78 (ddd, J=13.89, 10.16, 6.64 Hz, 1H) 3.05 (s, 3H) 3.33-3.41 (m, 1H) 3.46-3.54 (m, 1H) 4.22-4.37 (m, 2H).

Step C) Chiral separation of Ethyl 4-bromo-2-methyl-2-(methylsulfonyl)butanoate

Crude ethyl 4-bromo-2-methyl-2-(methylsulfonyl)butanoate (1.82 kg) was purified via flash chromatography using an LP-600 column and toluene as the eluent to afford pure ethyl 4-bromo-2-methyl-2-(methylsulfonyl)butanoate (1.63 kg). The purified material was dissolved in ethanol (75 g/L) and resolved via chiral column chromatography (conditions listed in Table 1) on MCC-2 to afford enantiomer #1 (738.4 g, rt=4.719 min, $[α]_{589}^{20}$=+14.1°) at 99% ee and enantiomer #2 (763.8 g, rt=4.040 min) at 95% ee. Purity of the enantiomers was determined via chiral HPLC, 4.6×250 mm Chiralpak AD, 10μ column, 215 nm wavelength, mobile phase: ethanol, isocratic elution at 1 mL/min at ambient temperature.

TABLE 1

| | |
|---|---|
| Stationary Phase | ChiralPak AD, 20 μ |
| Column Dimension/Temp | 5 × 10 cm/30° C. |
| Mobile Phase | 100% ethanol |
| Feed Concentration | 75 g/L in mobile phase |
| Feed Rate | 4.0 mL/min |
| Eluent Rate | 90.5 mL/min |
| Raffinate Rate | 35.6 mL/min |
| Extract Rate | 58.9 mL/min |
| Recycling Rate | 262 mL/min |
| Period Time | 1.0 min |

Enantiomer #1 was determined to be ethyl (2R)-4-bromo-2-methyl-2-(methylsulfonyl)butanoate, Template 1 (T1)

Preparation 2

The Scheme below illustrates the preparation of ethyl (2R)-4-(5-fluoro-4-iodo-2-oxopyridin-1(2H)-yl)-2-methyl-2-(methylsulfonyl)butanoate (T2) and (2R)-4-(5-fluoro-4-iodo-2-oxopyridin-1(2H)-yl)-2-methyl-2-(methylsulfonyl)-N-(tetrahydro-2H-pyran-2-yloxy)butanamide (T3) and the corresponding racemic and diastereomeric mixtures ethyl 4-(5-fluoro-4-iodo-2-oxopyridin-1(2H)-yl)-2-methyl-2-(methylsulfonyl)butanoate (T4) and 4-(5-fluoro-4-iodo-2-oxopyridin-1(2H)-yl)-2-methyl-2-(methylsulfonyl)-N-(tetrahydro-2H-pyran-2-yloxy)butanamide (T5).

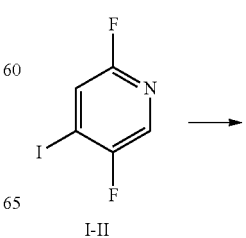

I-II

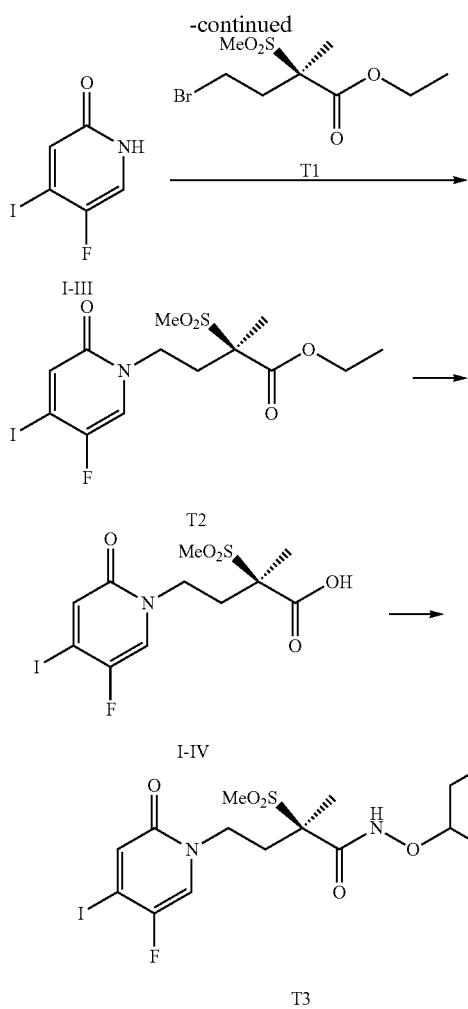

T3

Synthesis of Template 3 (T3): (2R)-4-(5-Fluoro-4-iodo-2-oxopyridin-1(2H)-yl)-2-methyl-2-(methylsulfonyl)-N-(tetrahydro-2H-pyran-2-yloxy)butanamide

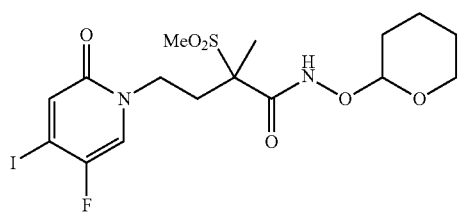 [SMILES: CC(CCn1cc(F)c(I)cc1=O)(C(=O)NOC1CCCCO1)S(C)(=O)=O]

Step A) Compound I-III:
5-Fluoro-4-iodopyridin-2(1H)-one

Concentrated HCl (50 mL) was added to a mixture of 2,5-difluoro-4-iodopyridine (2.0 g, 8.3 mmol) in 1,4-dioxane (350 mL) and water (100 mL). The mixture was heated to reflux and stirred at this temperature overnight. The reaction was concentrated to dryness and the residue was triturated in water (20 mL). The solids were collected via filtration and washed with water (2×30 mL) and hexanes (3×30 mL). The solid was dried under vacuum to afford the title compound as a yellow solid (1.0 g, 50%). MS (LCMS) m/z 240.0 (M+1). $^1$H NMR (400 MHz, DMSO-$d_6$) δ ppm 7.02 (d, J=5.07 Hz, 1H) 7.68 (d, J=2.34 Hz, 1H) 11.50 (br. s., 1H).

Step B) Template 2 (T2): Ethyl (2R)-4-(5-fluoro-4-iodo-2-oxopyridin-1(2H)-yl)-2-methyl-2-(methylsulfonyl)butanoate Cesium carbonate (1.77 g, 5.44 mmol) was added to a suspension of 5-fluoro-4-iodopyridin-2(1H)-one (1.00 g, 4.2 mmol) and ethyl (2R)-4-bromo-2-methyl-2-(methylsulfonyl)butanoate (1.56 g, 5.44 mmol) in anhydrous THF (45 mL). The reaction was heated to 70° C. and stirred at this temperature overnight. The reaction was quenched with water (100 mL) and extracted with EtOAc (2×100 mL). The combined organics were washed with brine (100 mL), dried (MgSO$_4$), filtered, and concentrated. The crude product was purified via flash chromatography using a Varian SF15-24g column and an eluent of EtOAc in n-heptane (30-80%) to afford the title compound as a yellow residue (691 mg, 37%). MS (LCMS) m/z 446.0 (M+1). $^1$H NMR (400 MHz, CHLOROFORM-d) δ ppm 1.36 (t, 3H) 1.75 (s, 3H) 2.37-2.57 (m, 2H) 3.10 (s, 3H) 3.83-4.02 (m, 1H) 4.16-4.37 (m, 3H) 7.15 (d, 1H) 7.20 (d, J=3.32 Hz, 1H).

Step C) Compound I-IV: (2R)-4-(5-Fluoro-4-iodo-2-oxopyridin-1(2H)-yl)-2-methyl-2-(methylsulfonyl)butanoic acid Potassium hydroxide (669 mg, 7.7 mmol) was added to a solution of ethyl (2R)-4-(5-fluoro-4-iodo-2-oxopyridin-1(2H)-yl)-2-methyl-2-(methylsulfonyl)butanoate (691 mg, 1.55 mmol) in 2-methyltetrahydrofuran:water (2:1, 22.5 mL) and the solution was stirred at 70° C. for 2 h. The reaction was diluted with 1 N aq NaOH (50 mL). The organics were separated and the aqueous layer was washed with EtOAc (2×50 mL), and acidified to a pH of 3 using 3 M aqueous HCl. The aqueous layer was extracted with EtOAc (3×60 mL), dried (MgSO$_4$), filtered and concentrated to afford a yellow-white solid (290 mg, 44.8%). MS (LCMS) m/z 418.0. $^1$H NMR (400 MHz, DMSO-$d_6$) δ ppm 1.53 (s, 3H) 2.08-2.20 (m, 1H) 2.36-2.48 (m, 1H) 3.13 (s, 3H) 3.79-4.02 (m, 2H) 7.03 (d, J=6.05 Hz, 1H) 7.96 (d, J=4.29 Hz, 1H) 13.82 (br. s., 1H).

Step D) Template 3 (T3): (2R)-4-(5-Fluoro-4-iodo-2-oxopyridin-1(2H)-yl)-2-methyl-2-(methylsulfonyl)-N-(tetrahydro-2H-pyran-2-yloxy)butanamide N-Methylmorpholine (120 uL, 1.1 mmol) was added to a solution of CDMT (178 mg, 1.01 mmol) and (2R)-4-(5-fluoro-4-iodo-2-oxopyridin-1(2H)-yl)-2-methyl-2-(methylsulfonyl)butanoic acid (280 mg, 0.762 mmol) in 2-methyltetrahydrofuran (7.60 mL) and the reaction was stirred at rt for 1 h. THP-hydroxylamine (117 mg, 1.00 mmol) was added to the reaction and the reaction was stirred overnight at rt. The reaction was quenched with water (50 mL) and the aqueous layer was extracted with EtOAc (3×50 mL). The combined organics were washed with brine (50 mL), dried (MgSO$_4$), filtered and concentrated to afford the title compound as an off-white solid (399.8 mg) MS (LCMS) 515.0 (M-1).

Example 1

(2R)-4-(5-fluoro-4-(2-fluoro-4-methoxyphenyl)-2-oxopyridin-1(2H)-yl)-2-methyl-2-(methylsulfonyl) butanamido phosphate

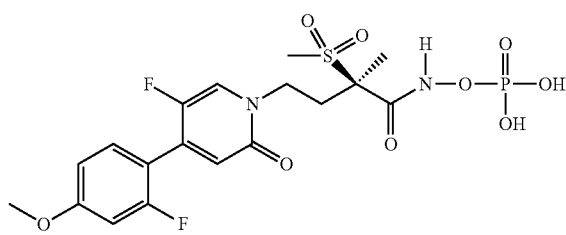 [SMILES: COc1ccc(-c2cc(=O)n(CC[C@](C)(C(=O)NOP(=O)(O)O)S(C)(=O)=O)cc2F)c(F)c1]

Step A) (2R)-4-[5-Fluoro-4-(2-fluoro-4-methoxyphenyl)-2-oxopyridin-1(2H)-yl]-2-methyl-2-(methylsulfonyl)-N-(tetrahydro-2H-pyran-2-yloxy)butanamide (2R)-4-[5-Fluoro-4-(2-fluoro-4-methoxyphenyl)-2-oxopyridin-1(2H)-yl]-2-methyl-2-(methylsulfonyl)-N-(tetrahydro-2H-pyran-2-yloxy)butanamide (1.5 g, 94%) was obtained from (2-fluoro-4-methoxyphenyl)boronic acid (737 mg, 4.34 mmol) and (2R)-4-(5-fluoro-4-iodo-2-oxopyridin-1(2H)-yl)-2-methyl-2-(methylsulfonyl)-N-(tetrahydro-2H-pyran-2-yloxy)butanamide, T3, (1.6 g, 3.1 mmol) in 1,4-dioxane:water. The reaction was heated to 80° C. and allowed to stir at this temperature overnight. The reaction was filtered through a pad of celite, which was washed with methanol. The filtrate was concentrated under reduced pressure, and the resulting crude material was purified via flash chromatography using an eluent of EtOAc in heptanes (20-100%), then 10% methanol in EtOAc to provide the title compound. MS (LCMS) m/z 513.3 (M+1).

Step B) (2R)-4-[5-Fluoro-4-(2-fluoro-4-methoxyphenyl)-2-oxopyridin-1(2H)-yl]-N-hydroxy-2-methyl-2-(methylsulfonyl)butanamide A solution of HCl (4 M in 1,4-dioxane, 4.4 mL, 17.5 mmol) was added to a solution of (2R)-4-[5-fluoro-4-(2-fluoro-4-methoxyphenyl)-2-oxopyridin-1(2H)-yl]-2-methyl-2-(methylsulfonyl)-N-(tetrahydro-2H-pyran-2-yloxy)butanamide (1.5 g, 2.9 mmol) in 1,4-dioxane (20 mL), DCM (20 mL), and water (5 mL) and the reaction was stirred for 20 min at rt. The reaction was concentrated under reduced pressure, isopropyl alcohol (10 mL) was added to the residue and the mixture was concentrated. Isopropyl alcohol (30 mL) was added to the residue and the solution was stirred overnight at rt to afford a precipitate. The precipitate was collected via filtration, washed with isopropyl alcohol, and dried under vacuum to afford the title compound as a light brown solid (725 mg, 58%) MS (LCMS) m/z 431.0 (M+1). $^1$H NMR (400 MHz, DMSO-$d_6$) δ ppm 1.57 (s, 3H) 2.07-2.25 (m, 1H) 2.42-2.48 (m, 1H) 3.11 (s, 3H) 3.71-3.81 (m, 1H) 3.83 (s, 3H) 4.00-4.11 (m, 1H) 6.44 (d, J=7.02 Hz, 1H) 6.92 (dd, J=8.59, 2.54 Hz, 1H) 7.00 (dd, J=12.39, 2.44 Hz, 1H) 7.42 (t, J=8.49 Hz, 1H) 8.03 (d, J=5.85 Hz, 1H) 9.25 (br. s., 1H) 11.10 (s, 1H).

Step C): (R)-4-(5-fluoro-4-(2-fluoro-4-methoxyphenyl)-2-oxopyridin-1(2H)-yl)-N-hydroxy-2-methyl-2-(methylsulfonyl)butanamide (5.00 g, 11.6 mmol) was dissolved in acetonitrile (80 mL) and N-methylmorpholine (5.93 g, 58.1 mmol) was added while stirring. The solution was cooled to −10° C. Phosphorus oxychloride (1.78 g, 11.6 mmol) was added over 30 seconds while stirring vigorously. The reaction was allowed to continue to stir for an additional 15 seconds and was then quenched with water (80 mL). The reaction was evaporated under reduced pressure to give 12.7 g of viscous oil which contains (2R)-4-(5-fluoro-4-(2-fluoro-4-methoxyphenyl)-2-oxopyridin-1(2H)-yl)-2-methyl-2-(methylsulfonyl)butanamido phosphate.

Example 2

(R)-4-(5-fluoro-4-(2-fluoro-4-methoxyphenyl)-2-oxopyridin-1(2H)-yl)-2-methyl-2-(methylsulfonyl) butanamido phosphate, diammonium salt

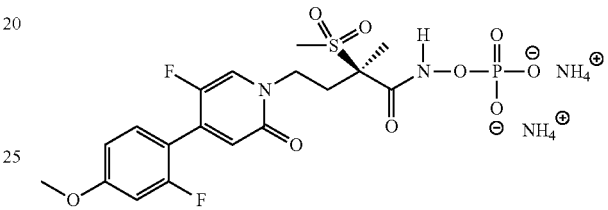

(R)-4-(5-fluoro-4-(2-fluoro-4-methoxyphenyl)-2-oxopyridin-1(2H)-yl)-N-hydroxy-2-methyl-2-(methylsulfonyl)butanamide (5.00 g, 11.6 mmol) was dissolved in acetonitrile (80 mL) and N-methylmorpholine (5.93 g, 58.1 mmol) was added while stirring. The solution was cooled to −10° C. Phosphorus oxychloride (1.78 g, 11.6 mmol) was added over 30 seconds while stirring vigorously. The reaction was allowed to continue to stir for an additional 15 seconds and was then quenched with water (80 mL). The reaction was evaporated under reduced pressure to give 12.7 g of viscous oil. A portion of this oil (6 g) was dissolved in acetonitrile (250 mL). While stirring, concentrated ammonium hydroxide solution (25 mL) was added to the solution over 5 minutes. The reaction was allowed to stir for 10 minutes and was collected and washed with additional acetonitrile (25 mL) and was dried to yield 1.78 g (61%) of an off-white solid. $^1$H NMR (500 MHz, D$_2$O) δ ppm 1.57 (br. s., 3H) 2.05-2.19 (m, 1H) 2.47 (t, J=10.13 Hz, 1H) 3.09 (br. s., 3H) 3.73 (br. s., 3H) 3.85 (t, J=10.50 Hz, 1H) 4.08-4.22 (m, 1H) 6.46 (d, J=5.98 Hz, 1H) 6.68-6.81 (m, 2H) 7.25 (t, J=8.30 Hz, 1H) 7.79 (br. s., 1H). [M$^+$ H]$^+$: 511.36.

Additional mass spectrometry and nuclear magnetic resonance studies were conducted in order to confirm the structure.

Mass Spectrometry Determination

A sample of (R)-4-(5-fluoro-4-(2-fluoro-4-methoxyphenyl)-2-oxopyridin-1(2H)-yl)-2-methyl-2-(methylsulfonyl) butanamido phosphate, diammonium salt, was dissolved in acetonitrile/water 80:20 (0.1 mg/mL). The sample was infused into the electrospray source. Accurate mass and fragmentation experiments were performed using the Waters Synpat G2 HDMS system in the negative mode. For accurate mass measurement, 2 μL of the sample was injected into a LC using a generic gradient and a flow rate of 0.4 mL/min. For fragmentation experiment, the same sample was directly infused into the mass spectrometer at a flow rate of 5 μL/min. A fragmentation energy of 10V was applied to observe the MS$^2$ spectrum. Further increase in fragmentation energy only resulted in the loss of precursor without any additional fragments. High resolution accurate mass measurements of (R)-4-(5-fluoro-4-(2-fluoro-4-methoxyphenyl)-2-oxopyridin-1(2H)-yl)-2-methyl-2-(methylsulfonyl) butanamido phosphate, diammonium salt showed the molecular ion (M−H)⁻ at m/z value of 509.0597 that correlates to a deprotonated empirical formula of $C_{18}H_{20}F_2N_2O_9PS$ with a deviation of 0.4 ppm from the theoretical mass. The MS² of m/z 509 gave fragments at m/z 97.0251 and 78.9596, which both relate to the phosphate leaving group which retains the negative charge (i.e. the fragment $H_2O_4P^-$ has an exact calculated mass of 96.9696 and the fragment $O_3P^-$ has an exact calculated mass of 78.9591).

NMR Study

Approximately 11 mg of sample was dissolved in 0.6 mL of 99.9% deuterated dimethyl sulfoxide (DMSO-d6) with 0.05% (v/v) tetramethylsilane (TMS). The 1D proton and 1D carbon spectra were referenced using the TMS signals, both set to 0.00 ppm. The 1D and 2D data were collected at 298K using a Bruker-Biospin 5 mm BBFO probe on a Bruker-Biospin AVANCE III NMR spectrometer operating at 500 MHz. The following data were collected: 1D proton, 1D carbon, 1H-1H gradient COSY (COrrelation SpectroscopY), 1H-13C multiplicity edited HSQC (Heteronuclear Single Quantum Coherence), 1H-13C HMBC (Heteronuclear Multiple Bond Correlation), 1H-1H NOESY (Nuclear Overhauser Effect SpectroscopY), and 1D phosphorous.

The 1D proton spectrum shows the expected chemical shifts, multiplicities, and integrations that are consistent with Structure 1. The 1D carbon spectrum is consistent with Structure 1 based upon chemical shift. The 2D spectra show the expected vicinal and geminal 1H-13C and 1H-1H correlations. Key homonuclear and heteronuclear correlations are indicated for the structure. Proton and carbon assignments are tabulated in Table 2. The NMR data are consistent with the structure shown herein. Stereochemistry of this compound is not explicitly evaluated. The phosphate group was determined to be on the N-hydroxyl site of the hydroxamic acid functionality. The carbon NMR data reveals that only one carbon resonance at 163.2 ppm (C-17) is coupled to the phosphorous atom with a coupling constant of 4.5 Hz. The adjacent carbon (C-16) was observed at 68.2 ppm with no splitting. Since carbon-phosphorous coupling for a phosphate group is similar for both 2-bond and 3-bond (around 4-8 Hz), the observed splitting is apparently a 3-bond coupling. Generally, a 4-bond coupling for carbon-phosphorous is 0 Hz. Therefore, the location of C-16 must be 4-bond away from the phosphorous atom.

The proton spectrum shows a large downfield peak of the exchangeable protons between 4.5 to 8.0 ppm. After the NMR sample was titrated with TFA, the water peak was observed at 4.26 ppm, ammonium peak at 7.15 ppm (the compound is an ammonium salt), and a downfield peak at 12.0 ppm with integration of one proton. Although very broad, the chemical shift of the 12.0 ppm peak is almost identical to that of the NH proton observed for (R)-4-(5-fluoro-4-(2-fluoro-4-methoxyphenyl)-2-oxo pyridin-1(2H)-yl)-N-hydroxy-2-methyl-2-(methylsulfonyl) butanamide, the parent compound of the phosphate ester (R)-4-(5-fluoro-4-(2-fluoro-4-methoxyphenyl)-2-oxopyridin-1(2H)-yl)-2-methyl-2-(methylsulfonyl)butanamido phosphate. This result provides further support for the structure.

TABLE 2

| Atom Number | 13C chemical shift (ppm) | ¹H chemical shift (ppm) | ¹H integral | ¹H multiplicity |
|---|---|---|---|---|
| 2 | 159.2 | — | — | — |
| 3 | 119.0 | 6.39 | 1 | d |
| 4 | 138.7, $J_{CF}$ = 18.8 Hz | — | — | — |
| 5 | 144.3, $J_{CF}$ = 229.2 Hz | — | — | — |
| 6 | 125.3, $J_{CF}$ = 39.2 Hz | 8.23 | 1 | d |
| 7 | 112.3, $J_{CF}$ = 15.5 Hz | — | — | — |
| 8 | 159.6, $J_{CF}$ = 248.1 Hz | — | — | — |
| 9 | 101.8, $J_{CF}$ = 25.5 Hz | 6.98 | 1 | dd |
| 10 | 161.8, $J_{CF}$ = 11.4 Hz | — | — | — |
| 11 | 110.9 | 6.90 | 1 | dd |
| 12 | 131.4, $J_{CF}$ = 3.8 Hz | 7.41 | 1 | t |
| 13 | 55.8 | 3.82 | 3 | s |
| 14 | 45.1 | 4.14, 3.91 | 1, 1 | m, m |
| 15 | 31.6 | 2.40, 2.16 | 1, 1 | m, m |
| 16 | 68.2 | — | — | — |
| 17 | 163.2, $^3J_{CP}$ = 4.5 Hz | — | — | — |
| 18 | — | n.o. | — | — |
| 19 | 15.2 | 1.51 | 3 | s |
| 20 | 36.9 | 3.11 | 3 | s | s = singlet, d = doublet, dd = doublet of doublets, t = triplet, m = multiplet, n.o. = not observed Example 3

(R)-4-(5-fluoro-4-(2-fluoro-4-methoxyphenyl)-2-oxopyridin-1(2H)-yl)-2-methyl-2-(methylsulfonyl) butanamido phosphate, Disodium Salt

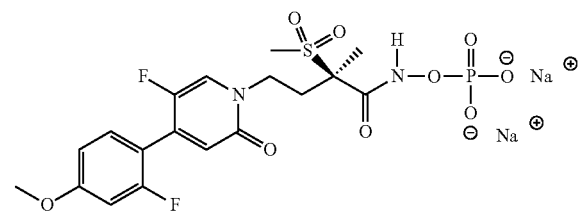 [SMILES: COc1ccc(-c2cc(=O)n(CC[C@](C)(C(=O)NOP(=O)([O-])[O-])S(C)(=O)=O)cc2F)c(F)c1 ; [Na+] ; [Na+]]

(R)-4-(5-fluoro-4-(2-fluoro-4-methoxyphenyl)-2-oxopyridin-1(2H)-yl)-N-hydroxy-2-methyl-2-(methylsulfonyl)butanamide (2.00 g, 4.7 mmol) was dissolved in acetonitrile (25 mL) and N-methylmorpholine (2.37 g, 23.2 mmol) was added. The solution was brought to −10° C. and the phosphorus oxychloride (0.71 g, 4.7 mmol) was added over the span of 30 seconds while stirring vigorously. The reaction was stirred for an additional 15 seconds, and then was quenched with water (25 mL). The reaction was evaporated and re-dissolved in acetonitrile (125 mL). 4M NaOH aqueous solution (30 mL, 100 mmol) was dropwise added while stirring. The aqueous layer was diluted with acetone (500 mL), producing a white precipitate, which was collected by vacuum filtration to give 1.98 g of an off-white solid (71%). ¹H NMR (400 MHz, D₂O) δ ppm 1.52 (s, 3H) 2.08 (td, J=12.07, 5.06 Hz, 1H) 2.46 (td, J=11.87, 4.28 Hz, 1H) 3.07 (s, 3H) 3.74 (s, 3H) 3.88 (td, J=12.26, 5.06 Hz, 1H) 4.19 (td, J=12.07, 5.06 Hz, 1H) 6.50 (d, J=6.62 Hz, 1H) 6.70-6.84 (m, 2H) 7.28 (t, J=8.76 Hz, 1H) 7.85 (d, J=5.45 Hz, 1H). [M+H]⁺: 511.28.

The solubility of the (R)-4-(5-fluoro-4-(2-fluoro-4-methoxyphenyl)-2-oxopyridin-1(2H)-yl)-2-methyl-2-(methylsulfonyl)butanamido phosphate, disodium salt is at least 20 mg/mL in normal saline whereas the parent compound (R)-4-(5-fluoro-4-(2-fluoro-4-methoxyphenyl)-2-oxopyridin-1(2H)-yl)-N-hydroxy-2-methyl-2-(methylsulfonyl) butanamide has a solubility of less than 1 mg/mL in normal saline. Thus, the (R)-4-(5-fluoro-4-(2-fluoro-4-methoxyphenyl)-2-oxopyridin-1(2H)-yl)-2-methyl-2-(methylsulfonyl) butanamido phosphate and salts thereof is suitable for a conventional intravenous formulation whereas the solubility of the parent (R)-4-(5-fluoro-4-(2-fluoro-4-methoxyphenyl)-2-oxopyridin-1(2H)-yl)-N-hydroxy-2-methyl-2-(methylsulfonyl) butanamide precludes formulation in a conventional intravenous vehicle.

General Procedure I for the Preparation of Salts

Dowex-50wx8-100 cation exchange resin is washed with water, methanol, and water again. The resin is then basified by treatment with an appropriate metal hydroxide (such as lithium hydroxide, potassium hydroxide, sodium hydroxide), ammonium hydroxide, amino acid or organic amine solution and is then washed with water. Divide the resin which is ready to use into three portions. To a solution of (R)-4-(5-fluoro-4-(2-fluoro-4-methoxyphenyl)-2-oxopyridin-1(2H)-yl)-2-methyl-2-(methylsulfonyl)butanamido phosphate salt (such as the ammonium or diammonium salt or the sodium or disodium salt) in water is added one portion of the resin. Stir the mixture for 10 minutes then filter it and rinse the solid with water. Add another portion of the resin to the combined filtrate and stir for 10 minutes, filter and rinse the solid with water. Add the final portion of resin, stir for 10 minutes, filter and rinse the solid with water. Concentrate the filtrate in vacuo, dissolve the residue in acetonitrile, filter, and concentrate the filtrate in vacuo. Dissolve the residue is methylene chloride, add hexane and concentrate in vacuo to provide the corresponding (R)-4-(5-fluoro-4-(2-fluoro-4-methoxyphenyl)-2-oxopyridin-1(2H)-yl)-2-methyl-2-(methylsulfonyl)butanamido phosphate mono or di salt.

The following Examples 4-8 can be prepared according to General Procedure 1.

Example 4: (R)-4-(5-fluoro-4-(2-fluoro-4-methoxyphenyl)-2-oxopyridin-1(2H)-yl)-2-methyl-2-(methylsulfonyl)butanamido phosphate, sodium salt Example 5: (R)-4-(5-fluoro-4-(2-fluoro-4-methoxyphenyl)-2-oxopyridin-1(2H)-yl)-2-methyl-2-(methylsulfonyl)butanamido phosphate, dilithium salt Example 6: (R)-4-(5-fluoro-4-(2-fluoro-4-methoxyphenyl)-2-oxopyridin-1(2H)-yl)-2-methyl-2-(methylsulfonyl)butanamido phosphate, lithium salt Example 7: (R)-4-(5-fluoro-4-(2-fluoro-4-methoxyphenyl)-2-oxopyridin-1(2H)-yl)-2-methyl-2-(methylsulfonyl)butanamido phosphate, dipotassium salt Example 8: (R)-4-(5-fluoro-4-(2-fluoro-4-methoxyphenyl)-2-oxopyridin-1(2H)-yl)-2-methyl-2-(methylsulfonyl)butanamido phosphate, potassium salt General Procedure II for the Preparation of Divalent Cation Salts One equivalent of (2R)-4-(5-fluoro-4-(2-fluoro-4-methoxyphenyl)-2-oxopyridin-1(2H)-yl)-2-methyl-2-(methylsulfonyl)butanamido phosphate is taken up in an appropriate solvent such as methanol at a concentration of approximately 10 mg/mL and is treated with one equivalent of the corresponding metal acetate (such as calcium acetate, zinc acetate or magnesium acetate). The resulting mixture is stirred at ambient temperature for several days then is concentrated in vacuo. The resulting residue is washed with a small amount of methanol and the product is dried.

The following Examples 9-11 can be prepared according to General Procedure II.

Example 9: (R)-4-(5-fluoro-4-(2-fluoro-4-methoxyphenyl)-2-oxopyridin-1(2H)-yl)-2-methyl-2-(methlsulfonyl)butanamido phosphate, calcium salt.

Example 10: (R)-4-(5-fluoro-4-(2-fluoro-4-methoxyphenyl)-2-oxopyridin-1(2H)-yl)-2-methyl-2-(methylsulfonyl)butanamido phosphate, magnesium salt.

Example 11: (R)-4-(5-fluoro-4-(2-fluoro-4-methoxyphenyl)-2-oxopyridin-1(2H)-yl)-2-methyl-2-(methylsulfonyl)butanamido phosphate, zinc salt.

General Procedure III for the Preparation of Monovalent Cation Salts

One equivalent of (2R)-4-(5-fluoro-4-(2-fluoro-4-methoxyphenyl)-2-oxopyridin-1(2H)-yl)-2-methyl-2-(methylsulfonyl)butanamido phosphate is taken up in an appropriate solvent such as methanol at a concentration of approximately 10 mg/mL and is treated with 1.0 to 1.1 equivalents of the appropriate corresponding amine (such as pyrrolidine, piperidine, pyridine, morpholine, piperazine, tris-(hydroxymethyl)methylamine, diethylamine, glycine). The resulting mixture is stirred at ambient temperature for several days then is concentrated in vacuo. The resulting residue is washed with a small amount of methanol and the product is dried. The following Examples 12-14 can be prepared according to General Procedure III Example 12: (R)-4-(5-fluoro-4-(2-fluoro-4-methoxyphenyl)-2-oxopyridin-1(2H)-yl)-2-methyl-2-(methylsulfonyl)butanamido phosphate, pyrrolidine salt.

Example 13: (R)-4-(5-fluoro-4-(2-fluoro-4-methoxyphenyl)-2-oxopyridin-1(2H)-yl)-2-methyl-2-(methylsulfonyl)butanamido phosphate, tris-(hydroxymethyl)methylamine salt.

Example 14: (R)-4-(5-fluoro-4-(2-fluoro-4-methoxyphenyl)-2-oxopyridin-1(2H)-yl)-2-methyl-2-(methylsulfonyl)butanamido phosphate, diethylamine salt.

Example 15: sodium (R)-5-(4-(5-fluoro-4-(2-fluoro-4-methoxyphenyl)-2-oxopyridin-1(2H)-yl)-2-(methylsulfonyl)butan-2-yl)-1,3,4,2-dioxazaborol-2-olate

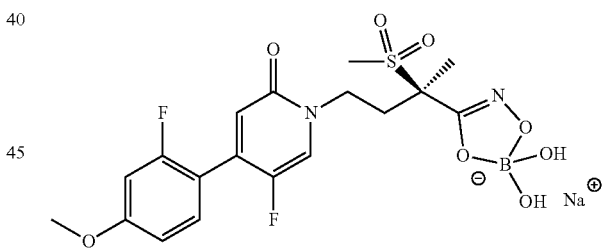

(R)-4-(5-fluoro-4-(2-fluoro-4-methoxyphenyl)-2-oxopyridin-1(2H)-yl)-N-hydroxy-2-methyl-2-(methylsulfonyl)butanamide (200 mg, 0.45 mmol) was suspended in water (30 mL). Boric acid (28 mg, 0.45 mmol) was added, followed by the sodium hydroxide (18 mg, 0.45 mmol). The reaction was allowed to stir at room temperature for approximately 30 minutes. The reaction solution was filtered via a teflon filter. The filtrate was transferred to a 250 mL round-bottom flask, where it was frozen at −78° C. The frozen solid was placed on a lyophilizer and was allowed to dry overnight (vacuum=0.2 mbar) to give 213 mg (99%) of a white powder. $^1$H NMR (400 MHz, D$_2$O) δ ppm 1.56 (s, 3H) 2.20 (td, J=12.03, 5.09 Hz, 1H) 2.44 (td, J=12.03, 5.09 Hz, 1H) 3.05 (s, 3H) 3.73 (s, 3H) 3.73-3.82 (m, 1H) 4.11 (td, J=11.98, 5.18 Hz, 1H) 6.47 (d, J=6.85 Hz, 1H) 6.69-6.78 (m, 2H) 7.24 (t, J=8.80 Hz, 1H) 7.68 (d, J=5.28 Hz, 1H). [M$^+$ H]+: 431.47 (parent).

Example 16: sodium (R)-5-(4-(5-fluoro-4-(2-fluoro-4-methoxyphenyl)-2-oxopyridin-1(2H)-yl)-2-(methylsulfonyl)butan-2-yl)-1,3,4,2-dioxazaborol-2-olate dimer

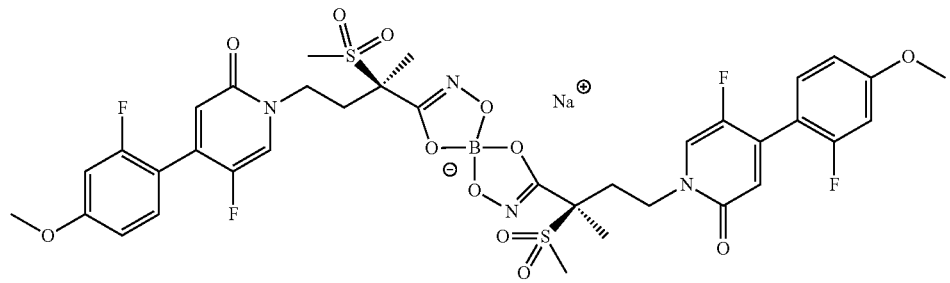

(R)-4-(5-fluoro-4-(2-fluoro-4-methoxyphenyl)-2-oxopyridin-1(2H)-yl)-N-hydroxy-2-methyl-2-(methylsulfonyl)butanamide (200 g) is combined with boric acid (29 g) and sodium hydroxide (18 g) in 1500 mL of water. The hazy solution is filtered and concentrated in vacuo to a thick oil. This is further dried by storage under high vacuum immersed in dry ice, for several days, to provide 224 g of monomeric boronate, sodium (R)-5-(4-(5-fluoro-4-(2-fluoro-4-methoxyphenyl)-2-oxopyridin-1(2H)-yl)-2-(methylsulfonyl)butan-2-yl)-1,3,4,2-dioxazaborol-2-oate as an amorphous solid.

The monomeric borate, sodium (R)-5-(4-(5-fluoro-4-(2-fluoro-4-methoxyphenyl)-2-oxopyridin-1(2H)-yl)-2-(methylsulfonyl)butan-2-yl)-1,3,4,2-dioxazaborol-2-olate (87.8 g) and (R)-4-(5-fluoro-4-(2-fluoro-4-methoxyphenyl)-2-oxopyridin-1(2H)-yl)-N-hydroxy-2-methyl-2-(methylsulfonyl)butanamide (77.6 g) are heated in 100 mL of THF for 30 minutes, until dissolved. The solution is cooled and filtered to remove haze. The filtrate is concentrated in vacuo to an oil, which foams to an amorphous solid under ~1 mm Hg vacuum to provide 168 g of the dimeric boronate as depicted above.

The crude dimeric isolate (330 g) is dissolved in 1500 mL of THF. To this is added slowly dropwise 1500 mL of pentane. An initially gummy precipitate soon becomes a well-stirred solid suspension. Continue to stir for 5 hours and collect the precipitate by suction filtration, washing with 500 mL of THF/pentane (1/1). Dry in a vacuum oven (45° C./22 in Hg) to provide 298 g of the dimeric boronate, depicted above as an amorphous solid. $^1$H NMR (DMSO-d$_6$; 400 MHz 5 (as a mixture of "cis/trans" isomers) 7.91 (d, J=5.85 Hz, 1H), 7.45 and 7.33 (t, J=8.59 Hz, 1H), 7.02-6.85 (m, 2H), 6.43 and 6.35 (d, J=7.4, 1H), 4.18-4.04 (m, 1H), 3.95-3.72 (m, 1H), 3.84 and 3.83 (s, 3H), 3.09 and 3.08 (s, 3H), 2.56-2.40 (m, 1H), 2.27-2.06 (m, 1H), 1.60 and 1.58 (s, 3H).

Biological Examples

In order to assess the compounds biological activity, selected in vitro assays were conducted on selected compounds. One of the assays measured the compounds ability to disrupt the synthesis of lipopolysaccharide, LPS, which is a component of the outer membrane of Gram-negative bacteria. Disruption of this synthesis is lethal to the bacteria. The assay determined the compound's ability to inhibit LpxC, which is the first enzyme in the biosynthetic pathway for LPS (measured as IC$_{50}$). Additionally, MICs (minimal inhibitory concentrations) were determined for several bacteria. The specific protocols are described below:

A) IC$_{50}$ Assay, LpxC Enzyme from *P. aeruginosa* (Labeled as PA LpxC Enzyme IC$_{50}$):

IC$_{50}$ determination in the LpxC enzyme assay was carried out in a similar manner to that described by Malikzay et al in the 2006 Poster, Screening LpxC (UDP-3-O—(R-3-hydroxymyristoyl)-GlcNAc deacetylase) using BioTrove RapidFire HTS Mass Spectrometry (aNew Lead Discovery and bInflammation and Infectious Disease, cStructural Chemistry, Schering-Plough Research Institute, Kenilworth, NJ 07033, (BioTrove, Inc. 12 Gill St., Suite 4000, Woburn, MA 01801). Briefly, *Pseudomonas aeruginosa* LpxC enzyme (0.1 nM) purified from *E. coli*-overexpressing bacteria was incubated at 25° C. in a final volume of 50 ul containing 0.5 uM UDP-3-O—(R-3-hydroxydecanoyl)-N-acetylglucosamine, 1 mg/mL BSA, and 50 mM sodium phosphate buffer, pH 8.0 in the presence and absence of inhibitor compound. At the end of 1 hour, 5 ul of 1 N HCl was added to stop the enzyme reaction, the plates were centrifuged, and then processed with the BioTrove Rapidfire HTMS Mass Spectrometry System. A no-enzyme control was used in calculating the IC$_{50}$ values from the percent conversion values.

B) MIC determinations: The in vitro antibacterial activity of compounds was evaluated by minimum inhibitory concentration (MIC) testing according to Clinical and Laboratory Standards Institute (CLSI). See: Clinical and Laboratory Standards Institute. Methods for Dilution Antimicrobial Susceptibility Tests for Bacteria that Grow Aerobically; Approved Standard-Eighth Edition. CLSI document M7-A8 [ISBN 1-56238-689-1]. Clinical and Laboratory Standards Institute, 940 West Valley Road, Suite 1400, Wayne, Pennsylvania 19087-1898 USA, 2006; also Clinical and Laboratory Standards Institute. Performance Standards for Antimicrobial Susceptibility Testing; Twentieth Informational Supplement. CLSI document M100-S20 [ISBN1-56238-716-2]. Clinical and Laboratory Standards Institute.

The MIC determination is a standard laboratory method for evaluating the antibacterial activity of a compound. The MIC represents the lowest drug concentration that inhibits visible growth of bacteria following overnight incubation. In order to determine the MIC value, a range of drug concentrations (e.g. 0.06 μg/mL to 64 μg/mL) are incubated with a defined strain of bacteria. Typically, the drug concentration range is broken down into 2-fold increments (e.g. 0.06 μg/mL, 0.12 μg/mL. 0.25 μg/mL, 0.50 μg/mL, 1.0 μg/mL, etc.) and the various drug concentrations are all individually incubated overnight with approximately the same number of bacteria. The MIC is then determined by visually inspecting the drug effect at each concentration, and identifying the lowest drug concentration that has inhibited bacterial growth as compared to the drug free control. Typically, bacteria continue to grow at drug concentrations lower than the MIC and don't grow at concentrations at and above the MIC.

The MIC values described in Table 3 below were derived from assays wherein each test compound was evaluated in duplicate. In cases where the duplicate values varied by 0-2-fold, the lower of the two values was reported below. Generally speaking, if the duplicate values varied by more than 2-fold, the assay was considered non-valid and was repeated until the variation between duplicate runs was s 2-fold. In line with the CLSI guidelines referred to above, both control organisms and reference compounds were utilized in each MIC assay to provide proper quality control. MIC values generated with these control organisms and reference compounds were required to fall within a defined range for the assay to be considered valid and be included herein. Those skilled in the art will recognize that MIC values can and do vary from experiment to experiment. Generally speaking, it should be recognized that MIC values often vary +/−2-fold from experiment to experiment. While a single MIC is reported for each compound and each microorganism, the reader should not conclude that each compound was only tested once. Several of the compounds were subjected to multiple tests. The data reported in Table 3 is reflective of the compounds relative activity and different MICs may have been generated on these occasions in line with the guidelines described above.

The following bacterial strains were used in these MIC determinations:
1) *Pseudomonas aeruginosa* UI-18: Wild-type, labeled as PA-7 in Table 3;
2) *Acinetobacter baumannii/haemolyticus*: Multidrug-resistant clinical isolate labeled as AB-3167 in Table 3;
3) *Escherichia coli* EC-1: VOGEL, mouse virulent labeled as EC-1 in Table 3;
4) *Klebsiella pneumoniae*: Ciprofloxacin-resistant isolate, expresses extended-spectrum beta-lactamases (ESBL), clinical isolate, labeled as KP-3700 in Table 3;

Table 3, below, shows the results that were obtained for the parent compound (2R)-4-[5-fluoro-4-(2-fluoro-4-methoxyphenyl)-2-oxopyridin-1(2H)-yl]-N-hydroxy-2-methyl-2-(methylsulfonyl)butanamide.

Column 1 corresponds to the Example number, column 2 provides the IUPAC name, column 3 provides the results from the LpxC enzyme assay described above, and columns 4-7 provide the MIC data as described above.

observed that the (2R)-4-[5-fluoro-4-(2-fluoro-4-methoxyphenyl)-2-oxopyridin-1(2H)-yl]-N-hydroxy-2-methyl-2-(methylsulfonyl) butanamide phosphate disappeared, concomitant with appearance of (2R)-4-[5-fluoro-4-(2-fluoro-4-methoxyphenyl)-2-oxopyridin-1(2H)-yl]-N-hydroxy-2-methyl-2-(methylsulfonyl) butanamide (parent compound) and a glucuronide metabolite of the parent compound.

In Vivo Studies

In vivo efficacy of (2R)-4-[5-fluoro-4-(2-fluoro-4-methoxyphenyl)-2-oxopyridin-1(2H)-yl]-N-hydroxy-2-methyl-2-(methylsulfonyl)butanamide phosphate and (2R)-4-[5-fluoro-4-(2-fluoro-4-methoxyphenyl)-2-oxopyridin-1(2H)-yl]-N-hydroxy-2-methyl-2-(methylsulfonyl) butanamide boronate.

The in vivo efficacy of (2R)-4-[5-fluoro-4-(2-fluoro-4-methoxyphenyl)-2-oxopyridin-1(2H)-yl]-N-hydroxy-2-methyl-2-(methylsulfonyl)butanamide (parent compound), (2R)-4-[5-fluoro-4-(2-fluoro-4-methoxyphenyl)-2-oxopyridin-1(2H)-yl]-N-hydroxy-2-methyl-2-(methylsulfonyl)butanamide phosphate and (2R)-4-[5-fluoro-4-(2-fluoro-4-methoxyphenyl)-2-oxopyridin-1(2H)-yl]-N-hydroxy-2-methyl-2-(methylsulfonyl) butanamide boronate, was determined using the murine neutropenic lung infection model as described in Seth T. Housman, Jared L. Crandon, Wright W. Nichols and David P. Nicolau; *Antimicrob. Agents Chemother.* 2014, 58(3):1365.

Neutropenic Lung Infection Model.

Pathogen-free female ICR mice weighing approximately 25 g were acquired from Harlan Laboratories (Indianapolis, IN). This study was reviewed and approved by the Hartford Hospital Institutional Animal Care and Use Committee. Animals were maintained and used in accordance with National Research Council recommendations and were provided food and water ad libitum. Mice were rendered neutropenic by administering intraperitoneal injections of cyclophosphamide (Baxter, Deerfield, IL) at doses of 250 and 100 mg/kg body weight 4 days and 1 day, respectively, prior to inoculation. Uranyl nitrate at a dose of 5 mg/kg was also administered 3 days prior to inoculation to induce renal impairment. Mice were anesthetized with isoflurane and inoculated with 0.05 mL of a 107-CFU/ml suspension of the infecting *P. aeruginosa* isolate in 3% porcine stomach mucin (Sigma-Aldrich, St. Louis, MO). The inoculum was administered into the mouths of the mice while blocking their nares to induce aspiration The in vivo efficacy of (2R)-4-[5-fluoro-4-(2-fluoro-4-methoxyphenyl)-2-oxopyridin-1(2H)-yl]-N-hydroxy-2-methyl-2-(methylsulfonyl)butanamide (parent compound), (2R)-4-[5-fluoro-4-(2-fluoro-4-methoxyphenyl)-2-oxopyridin-1(2H)-yl]-N-hydroxy-2-methyl-2-(methylsulfonyl)butanamide phosphate and (2R)-4-[5-fluoro-4-(2-fluoro-4-methoxyphenyl)-2-oxopyridin-1

TABLE 3

| Example | IUPAC NAME | PA: IC50 (µM) | AB-3167 (µg/mL) | EC-1 (µg/mL) | KP-3700 (µg/mL) | PA-7 (µg/mL) |
|---|---|---|---|---|---|---|
| Parent Compound | (2R)-4-[5-fluoro-4-(2-fluoro-4-methoxyphenyl)-2-oxopyridin-1(2H)-yl]-N-hydroxy-2-methyl-2-(methylsulfonyl)butanamide | 0.0000498 | >64.0 | 0.25 | 0.5 | 0.5 |

In vitro hepatocyte study: The disposition of (2R)-4-[5-fluoro-4-(2-fluoro-4-methoxyphenyl)-2-oxopyridin-1(2H)-yl]-N-hydroxy-2-methyl-2-(methylsulfonyl) butanamide phosphate was examined in hepatocytes from mouse, rat, dog, monkey and human. In each case, qualitatively it was (2H)-yl]-N-hydroxy-2-methyl-2-(methylsulfonyl) butanamide boronate LPXC1, was determined using the murine neutropenic lung infection model against two strains of *Pseudomonas aeruginosa* and one of *Klebsiella pneumoniae* after 24 hours of treatment.

(2R)-4-[5-fluoro-4-(2-fluoro-4-methoxyphenyl)-2-oxopyridin-1(2H)-yl]-N-hydroxy-2-methyl-2-(methylsulfonyl)butanamide (parent compound) had in vitro microbiological activity against all species with MIC levels of 0.5 to 1 g/mL. Two hours after inoculation, groups of 3 animals were given total daily doses of 25 to 600 mg/kg as two- or four-times daily regimens via subcutaneous administration. Efficacy was determined as the change in bacterial density in treated animals after 24 hours of therapy as compared with that of control animals at the initiation of dosing.

All three compounds had antibacterial effects in vivo resulting in 2-4 log decreases in bacterial density against the *P. aeruginosa* isolates. The effects of the compounds against the *K. pneumoniae* isolate did not readily reach maximal effects, despite the use of higher doses and were quite variable as compared with the *P. aeruginosa* strains. Given earlier observations of efficacy against this organism with (2R)-4-[5-fluoro-4-(2-fluoro-4-methoxyphenyl)-2-oxopyridin-1(2H)-yl]-N-hydroxy-2-methyl-2-(methylsulfonyl)butanamide itself, additional studies with other *Klebsiella* strains would be needed to fully understand in vivo efficacy against this pathogen.

What is claimed is:

1. A compound of Formula I:

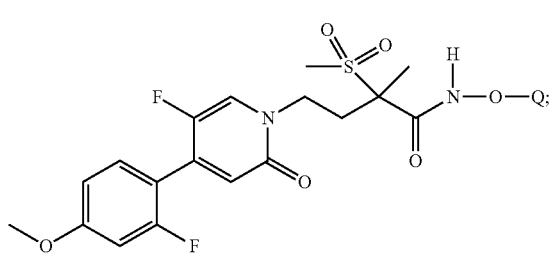

wherein Q is selected from the group consisting of —P(O)(OH)$_2$, —P(O)(OH)(O$^-$M$^+$), —P(O)(O$^-$M$^+$)$_2$ and —P(O)(O$^-$)$_2$M$^{2+}$;

M$^+$ at each occurrence is a pharmaceutically acceptable monovalent cation; and M$^{2+}$ is a pharmaceutically acceptable divalent cation.

2. The compound according to claim 1 of Formula Ia:

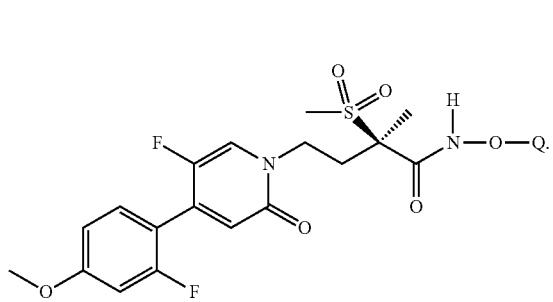

3. The compound according to claim 2 wherein Q is —P(O)(OH)$_2$.

4. The compound according to claim 2 wherein Q is —P(O)(OH)(O$^-$M$^+$), or —P(O)(O$^-$M$^+$)$_2$.

5. The compound according to claim 4 wherein Q is —P(O)(O$^-$M$^+$)$_2$.

6. The compound according to claim 2 wherein Q is —P(O)(O$^-$)$_2$M$^{2+}$.

7. The compound according to claim 4 wherein M$^+$ at each occurrence is independently selected from the group consisting of Li$^+$, K$^+$ and Na$^+$.

8. The compound according to claim 4 wherein M$^+$ at each occurrence is a pharmaceutically acceptable monovalent cation independently selected from ammonium, (C$_1$-C$_{12}$alkyl)ammonium, (C$_1$-C$_{12}$alkyl)$_2$ammonium, (C$_1$-C$_{12}$alkyl)$_3$ammonium, (C$_1$-C$_{12}$alkyl)$_4$ammonium, (C$_3$-C$_6$cycloalkyl)ammonium, (C$_3$-C$_6$cycloalkyl)$_2$ammonium, (C$_3$-C$_6$cycloalkyl)$_3$ammonium, (C$_3$-C$_6$cycloalkyl)$_4$ammonium, pyrrolidinium, piperidinium and pyridinium; wherein each of the (C$_1$-C$_{12}$alkyl) or (C$_3$-C$_6$cycloalkyl) moieties are optionally substituted with one to three hydroxy or halo.

9. The compound according to claim 4 wherein M$^+$ at each occurrence is a pharmaceutically acceptable monovalent cation independently selected from the group consisting of glycinium, alaninium, β-alaninium, valinium, lysinium, isoleucinium, leucinium, methioninium, threoninium, asparaginium, glutaminium, histidinium, argininium, ornithinium, tryptophanium, prolinium, glutaminium, cysteinium, phenylalaninium, tyrosinium and serinium.

10. The compound according to claim 4 of the formula

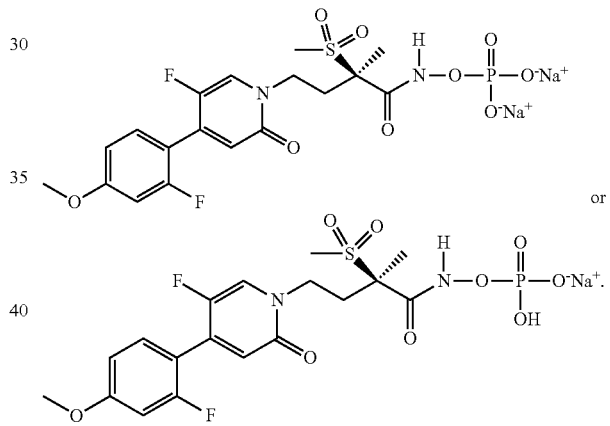

11. The compound according to claim 4 of the formula

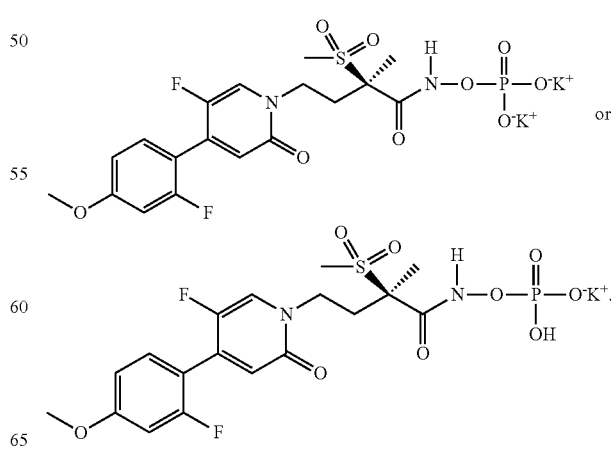

12. The compound according to claim 4 of the formula
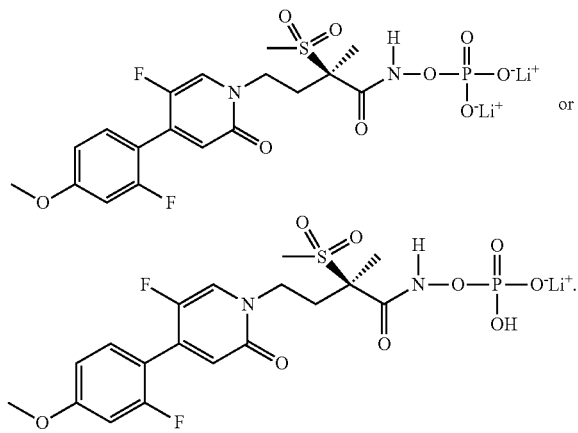
or
13. The compound according to claim 4 of the formula
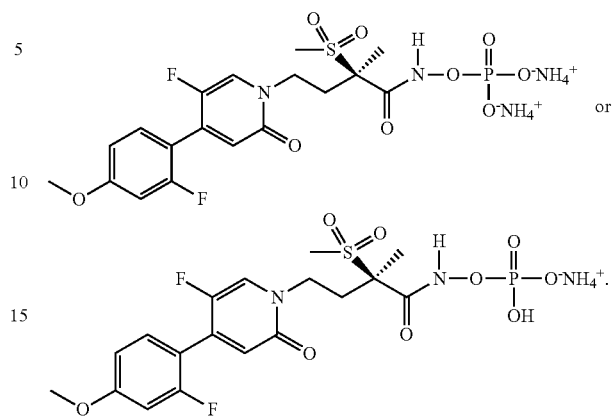
or
14. The compound according to claim 4 of the formula
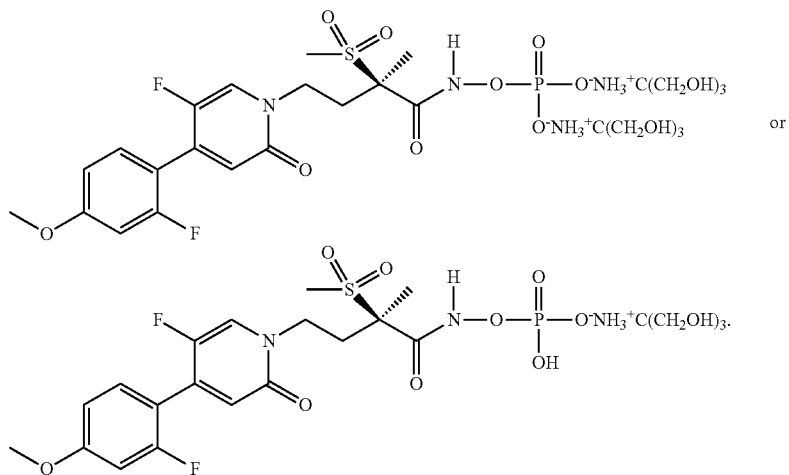
or
15. The compound according to claim 4 of the formula
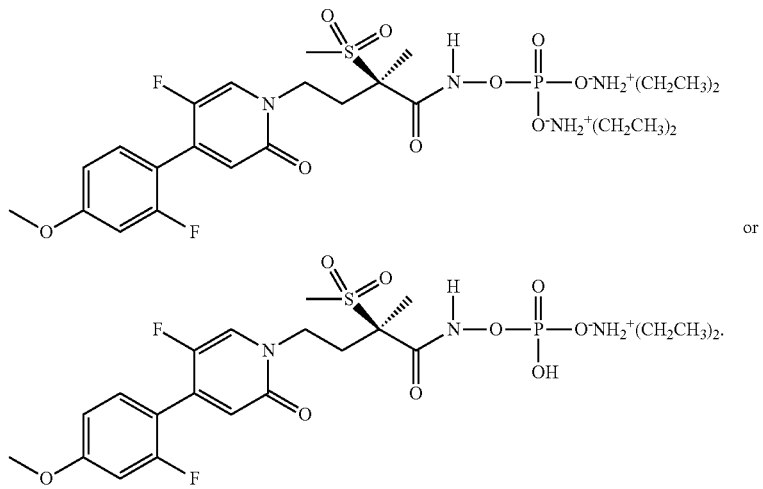

16. The compound according to claim 6 wherein $M^{2+}$ is selected from the group consisting of $Ca^{2+}$, $Mg^{2+}$ and $Zn^{2+}$.

17. A pharmaceutical composition comprising a compound according to claim 1 in admixture with at least one pharmaceutically acceptable excipient.

18. A method for a treating a Gram-negative bacterial infection in a patient, the method comprising administering a therapeutically effective amount of a compound according to claim 1 to a patient in need thereof.

* * * * *